(12) United States Patent
Wang et al.

(10) Patent No.: US 7,132,439 B2
(45) Date of Patent: Nov. 7, 2006

(54) BIS-BENZIMIDAZOLES AND RELATED COMPOUNDS AS POTASSIUM CHANNEL MODULATORS

(75) Inventors: Xiaodong Wang, Chapel Hill, NC (US); Alan B. Fulp, Willow Springs, NC (US); Albert M. van Rhee, Durham, NC (US); Kerry L. Spear, Raleigh, NC (US)

(73) Assignee: Icagen, Inc., Durham, NC (US)

( * ) Notice: Subject to any disclaimer, the term of this patent is extended or adjusted under 35 U.S.C. 154(b) by 16 days.

(21) Appl. No.: 10/437,732

(22) Filed: May 13, 2003

(65) Prior Publication Data

US 2004/0029925 A1    Feb. 12, 2004

Related U.S. Application Data

(60) Provisional application No. 60/380,367, filed on May 13, 2002.

(51) Int. Cl.
| | | |
|---|---|---|
| A61K 31/4164 | (2006.01) | |
| A61K 31/421 | (2006.01) | |
| C07D 235/04 | (2006.01) | |
| C07D 403/10 | (2006.01) | |

(52) U.S. Cl. .................. 514/393; 548/148; 548/152; 548/159; 548/215; 548/217; 548/304.4; 548/305.4; 514/385; 514/393; 514/374; 514/375

(58) Field of Classification Search ............. 548/304.4, 548/305.4, 152, 217; 514/393, 385, 375
See application file for complete search history.

(56) References Cited

U.S. PATENT DOCUMENTS 3,250,780 A * 5/1966 Rai et al. .................... 548/219
3,621,076 A * 11/1971 De Winter et al. ......... 525/432
5,922,794 A     7/1999 Prabhu et al.
6,627,180 B1 * 9/2003 Candau ....................... 424/59

FOREIGN PATENT DOCUMENTS

| WO | WO 00/01676 A1 | 1/2000 |
| WO | WO 02/49597 | * 6/2002 |

OTHER PUBLICATIONS

Arient et al (1963): STN International CAPLUS database, Columbus (Ohio), Accession No. 1963:436047.*
Preston et al (1993): STN International CAPLUS database, Columbus (Ohio), Accession No. 1993:214076.*
Candau Didier (2002): STN International CAPLUS database, Columbus (Ohio), Accession No. 2002:487357.*
Berrada M. et al., "Synthisis, Characterization, and Studies of Heat-Resistant Poly(ether benzimidazole)s"; 1997, *Chem. Mater.*, vol. 9, pp. 1989-1993.
Wang, Lillian Li-Yen et al.; "Synthesis of Bis-benzimidazoles"; 1957, *Journal of the American Chemical Society*, vol. 79, pp. 5703-5708.

* cited by examiner

*Primary Examiner*—Golam M. M. Shameem
(74) *Attorney, Agent, or Firm*—Townsend and Townsend and Crew LLP

(57) ABSTRACT

The present invention provides a genus of bis-benzimidazole compounds, methods and pharmaceutical compositions that are useful as modulators of potassium ion channels. The compounds of the invention are of use in both therapeutic and diagnostic methods.

10 Claims, 6 Drawing Sheets

BIS-BENZIMIDAZOLES AND RELATED COMPOUNDS AS POTASSIUM CHANNEL MODULATORS

CROSS-REFERENCE TO RELATED APPLICATIONS

This is a non-provisional filing of U.S. provisional patent application No. 60/380,367, filed on May 13, 2002, the disclosure of which is incorporated herein by reference in its entirety for all purposes.

FIELD OF THE INVENTION

This invention relates to the use of certain bis-benzimidazole compounds as potassium channel modulators and to the treatment of diseases by the modulation of potassium channels. Additionally, this invention relates to novel bis-benzimidazole compounds that are useful as potassium channel modulators.

BACKGROUND OF THE INVENTION

Ion channels are cellular proteins that regulate the flow of ions, including calcium, potassium, sodium and chloride, into and out of cells. These channels are present in all human cells and affect such processes as nerve transmission, muscle contraction and cellular secretion. Among the ion channels, potassium channels are the most ubiquitous and diverse, being found in a variety of animal cells such as nervous, muscular, glandular, immune, reproductive, and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands, and ATP-sensitivity.

Potassium channels have now been associated with a number of physiological processes, including regulation of heartbeat, dilation of arteries, release of insulin, excitability of nerve cells, and regulation of renal electrolyte transport. Moreover, studies have indicated that $K^+$ channels are a therapeutic target in the treatment of a number of diseases including central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, psychosis, anxiety, depression, dementia, memory and attention deficits, Alzheimer's disease, age-related memory loss, learning deficiencies, anxiety, traumatic brain injury, dysmenorrhea, narcolepsy and motor neuron diseases), as well as targets for neuroprotective agents (e.g., to prevent stroke and the like). The compounds of the invention are also useful in treating disease states such as gastroesophogeal reflux disorder and gastrointestinal hypomotility disorders, irritable bowel syndrome, secretory diarrhea, asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, ischemia, cerebral ischemia, ischemic heart disease, angina pectoris, coronary heart disease, Reynaud's disease, intermittent claudication, Sjorgren's syndrome, arrhythmia, hypertension, myotonic muscle dystrophia, xerostomi, diabetes type II, hyperinsulinemia, premature labor, baldness, cancer, and immune suppression.

Potassium channels are made by alpha subunits that fall into at least 8 families, based on predicted structural and functional similarities (Wei et al., *Neuropharmacology* 35(7): 805–829 (1997)). Three of these families (Kv, eag-related, and KQT) share a common motif of six transmembrane domains and are primarily gated by voltage. Two other families, CNG and SK/IK, also contain this motif but are gated by cyclic nucleotides and calcium, respectively. The three other families of potassium channel alpha subunits have distinct patterns of transmembrane domains. Slo family potassium channels, or BK channels have seven transmembrane domains (Meera et al., *Proc. Natl. Acad. Sci. U.S.A.* 94(25): 14066–14071 (1997)) and are gated by both voltage and calcium or pH (Schreiber et al., *J. Biol. Chem.* 273: 3509–3516 (1998)). Another family, the inward rectifier potassium channels (Kir), belong to a structural family containing two transmembrane domains, and an eighth functionally diverse family (TP, or "two-pore") contains two tandem repeats of this inward rectifier motif.

Potassium channels are typically formed by four alpha subunits, and can be homomeric (made of identical alpha subunits) or heteromeric (made of two or more distinct types of alpha subunits). In addition, potassium channels made from Kv, KQT and Slo or BK subunits have often been found to contain additional, structurally distinct auxiliary, or beta, subunits. These subunits do not form potassium channels themselves, but instead they act as auxiliary subunits to modify the functional properties of channels formed by alpha subunits. For example, the Kv beta subunits are cytoplasmic and are known to increase the surface expression of Kv channels and/or modify inactivation kinetics of the channel (Heinemann et al., *J. Physiol.* 493: 625–633 (1996); Shi et al., *Neuron* 16(4): 843–852 (1996)). In another example, the KQT family beta subunit, minK, primarily changes activation kinetics (Sanguinetti et al., *Nature* 384: 80–83 (1996)).

Slo or BK potassium channels are large conductance potassium channels found in a wide variety of tissues, both in the central nervous system and periphery. They play a key role in the regulation of processes such as neuronal integration, muscular contraction and hormone secretion. They may also be involved in processes such as lymphocyte differentiation and cell proliferation, spermatocyte differentiation and sperm motility. Three alpha subunits of the Slo family have been cloned, i.e., Slo1, Slo2, and Slo3 (Butler et al., *Science* 261: 221–224 (1993); Schreiber et al., *J. Biol. Chem.*, 273: 3509–16 (1998); and Joiner et al., *Nature Neurosci.* 1: 462–469 (1998)). These Slo family members have been shown to be voltage and/or calcium gated, and/or regulated by intracellular pH.

Certain members of the Kv family of potassium channels were recently renamed (see, Biervert, et al., *Science* 279: 403–406 (1998)). KvLQT1 was re-named KCNQ1, and the KvLQT1-related channels (KvLR1 and KvLR2) were renamed KCNQ2 and KCNQ3, respectively. More recently, a fourth member of the KCNQ subfamily was identified (KCNQ4) as a channel expressed in sensory outer hair cells (Kubisch, et al., *Cell* 96(3): 437–446 (1999)).

SK channels are small conductance, $Ca^{2+}$-activated $K^+$ channels that underlie neuronal slow afterhyperpolarization and mediate spike frequency adaptation (Khawaled et al., *Pflugers Arch.* 438: 314–321 (1999)). SK channels are present in many central neurons and ganglia, where their primary function is to hyperpolarize nerve cells following one or several action potentials, in order to prevent the occurrence of long trains of epileptogenic activity. The SK channels are also present in several peripheral cells including skeletal muscle, gland cells, liver cells, and T-lymphocytes. The significance of SK channels in normal skeletal muscle is not clear, but their number is significantly increased in denervated muscle, and the large number of SK channels in the muscle of patients with myotonic muscle dystrophia suggests a role in the pathogenesis of the disease.

Three SK channels have been identified to date: SK1, SK2 and SK3 (Rimini et al., *Brain Res. Mol. Brain Res.* 85: 218–220 (2000)). The quantities of SK1, SK2 and SK3 expression in human brain have been measured using TaqMan RT-PCR on a range of human brain and peripheral tissue samples. SK1 expression was found to be restricted to the brain whereas SK2 and SK3 are more widely expressed.

SK channels have been shown to have a distinct pharmacological profile. For example, using patch clamp techniques, the effects on SK2 subtype channels of eight clinically relevant psychoactive compounds structurally related to the tricyclic antidepressants were investigated (Dreixler et al., *Eur. J. Pharmacol.* 401: 1–7 (2000)). The compounds evaluated included amitriptyline, carbamazepine, chlorpromazine, cyproheptadine, imipramine, tacrine and trifluperazine. Each of the compounds tested was found to block SK2 channel currents with micromolar affinity. In contrast, the cognitive enhancer linopirdine was ineffective at inhibiting SK channels. A number of neuromuscular inhibiting agents which affect SK channels exist, e.g. apamin, atracurium, pancuronium and tubocurarine (Shah et al., *Br J Pharmacol* 129: 627–30 (2000)).

Patch clamp techniques have been used to study the effect of the centrally acting muscle relaxant chlorzoxazone and three structurally related compounds, 1-ethyl-2-benzimidazolinone (1-EBIO), zoxazolamine, and 1,3-dihydro-1-[2-hydroxy-5-(trifluoromethyl)phenyl]-5-(trifluoromethyl)-2H-benzimidazol-2-one (NS 1619) on recombinant rat brain SK2 channels (rSK2 channels) expressed in HEK293 mammalian cells (Cao et al., *J Pharmacol Exp. Ther.* 296: 683–689 (2001)). When applied externally, chlorzoxazone, 1-EBIO, and zoxazolamine activated rSK2 channel currents in cells dialyzed with a nominally $Ca^{2+}$-free intracellular solution.

The effects of metal cations on the activation of recombinant human SK4 (also known as hIK1 or hKCa4) channels has also been studied (Cao and Houamed, *FEBS Lett.* 446: 137–141 (1999)). The ion channels were expressed in HEK 293 cells, and tested using patch clamp recording. Of the nine metals tested, cobalt, iron, magnesium, and zinc did not activate the SK4 channels when applied, at concentrations up to 100 μM, to the inside of SK4 channel-expressing membrane patches. Barium, cadmium, calcium, lead, and strontium activated SK4 channels in a concentration-dependent manner. The rank order of potency was at $Ca^{2+}>Pb^{2+}>Cd^{2+}>Sr^{2+}>Ba^{2+}$.

WO 97/48705 discloses a particular group of chemical compounds useful as calcium activated potassium channel inhibiting agents. U.S. Pat. No. 5,739,127 and U.S. Pat. No. 5,760,230 discloses a series of 2,4'-bridged bis-2,4-diaminoquinazolines having activity towards apamine-sensitive potassium channels. None of the aforementioned references disclose that the compounds set forth therein exhibit any selectivity towards the SK channel.

WO 00/01676 discloses a genus of potassium channel inhibiting agents based on an amine-substituted bis-benzimidazole scaffold in which the amine-substituted benzimidazole moieties are joined by a linker arm. Similar compounds are set forth in U.S. Pat. No. 5,922,794. Each of the disclosed bis-benzimidazoles is derivatized at one or more of the endocyclic imidazole nitrogen atoms Moreover, the majority of the disclosed bis-benzimidazole compounds include a linker arm that is attached to either an endocyclic amine moiety or to the amine substituent of the amine-substituted benzimidazole subunits.

In contrast to the compounds set forth in WO 00/01676, and U.S. Pat. No. 5,922,794, the present invention provides a genus of SK channel modulators that are based on a bis-benzimidazole scaffold in which the benzimidazole moieties are linked through the carbon atom at position-2 of the imidazole ring system. The compounds of the invention are potent and specific modulators of SK channels.

SUMMARY OF THE INVENTION

The present invention provides bis-benzimidazole compounds, which are useful in modulating potassium ion flux through voltage-dependent potassium channels, and for treating diseases through the modulation of potassium ion flux through these channels. The compounds of the invention have a novel structural motif in which the benzimidazole units are joined through a linker group bound to the C-2 carbon of at least one of the benzimidazole units.

More particularly, the invention provides compounds, compositions and methods that are useful in the treatment of central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, psychosis, anxiety, depression, dementia, memory and attention deficits, Alzheimer's disease, age-related memory loss, learning deficiencies, anxiety, traumatic brain injury, dysmenorrhea, narcolepsy and motor neuron diseases), as well as active as neuroprotective agents (e.g., to prevent stroke and the like). The compounds of the invention are also useful in treating disease states such as gastroesophogeal reflux disorder and gastrointestinal hypomotility disorders, irritable bowel syndrome, secretory diarrhea, asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, ischemia, cerebral ischemia, ischemic heart disease, angina pectoris, coronary heart disease, Reynaud's disease, intermittent claudication, Sjorgren's syndrome, arrhythmia, hypertension, myotonic muscle dystrophia, xerostomi, diabetes type II, hyperinsulinemia, premature labor, baldness, cancer, and immune suppression.

In one aspect, the present invention provides compounds having a structure according to Formula I:

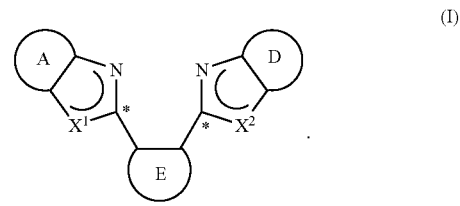

(I)

In Formula I, ring systems A, D and E are independently selected from substituted or unsubstituted aryl, and substituted or unsubstituted heteroaryl ring systems. The symbols $X^1$ and $X^2$ independently represent $NR^1$, S, O, $NHC(R^2)$, $SC(R^3)$, $OC(R^4)$, and $C(R^5)$. $R^1$, $R^2$, $R^3$, $R^4$, and $R^5$ independently represent H and substituted or unsubstituted alkyl, substituted or unsubstituted arylalkyl and substituted or unsubstituted heteroaryl. The semicircular bond within the heterocyclic ring system indicates that a double bond may be located between the carbon marked * and N or this carbon and $X^1$ or, alternatively $X^2$.

The invention also provides pharmaceutical compositions that include one or more compounds of the invention in combination with a pharmaceutically acceptable excipient.

Also provided by the present invention are methods for modulating ion flow through voltage-dependent potassium channels in a cell. The method includes contacting the cell with a potassium channel-modulating amount of a compound of the invention. The cell may be in culture or in a subject in need of treatment that involves modulating ion flow through a voltage-dependent channel.

In a further aspect, the invention provides a method of treating a disorder or condition through modulation of a voltage-dependent potassium channel of the SK family. The method includes administering a therapeutically effective amount of a compound of the invention to a subject in need of such treatment.

Other objects, advantages and embodiments of the invention will be apparent from review of the Detailed Description that follows.

DETAILED DESCRIPTION OF THE INVENTION AND THE PREFERRED EMBODIMENTS

Figure 1A:
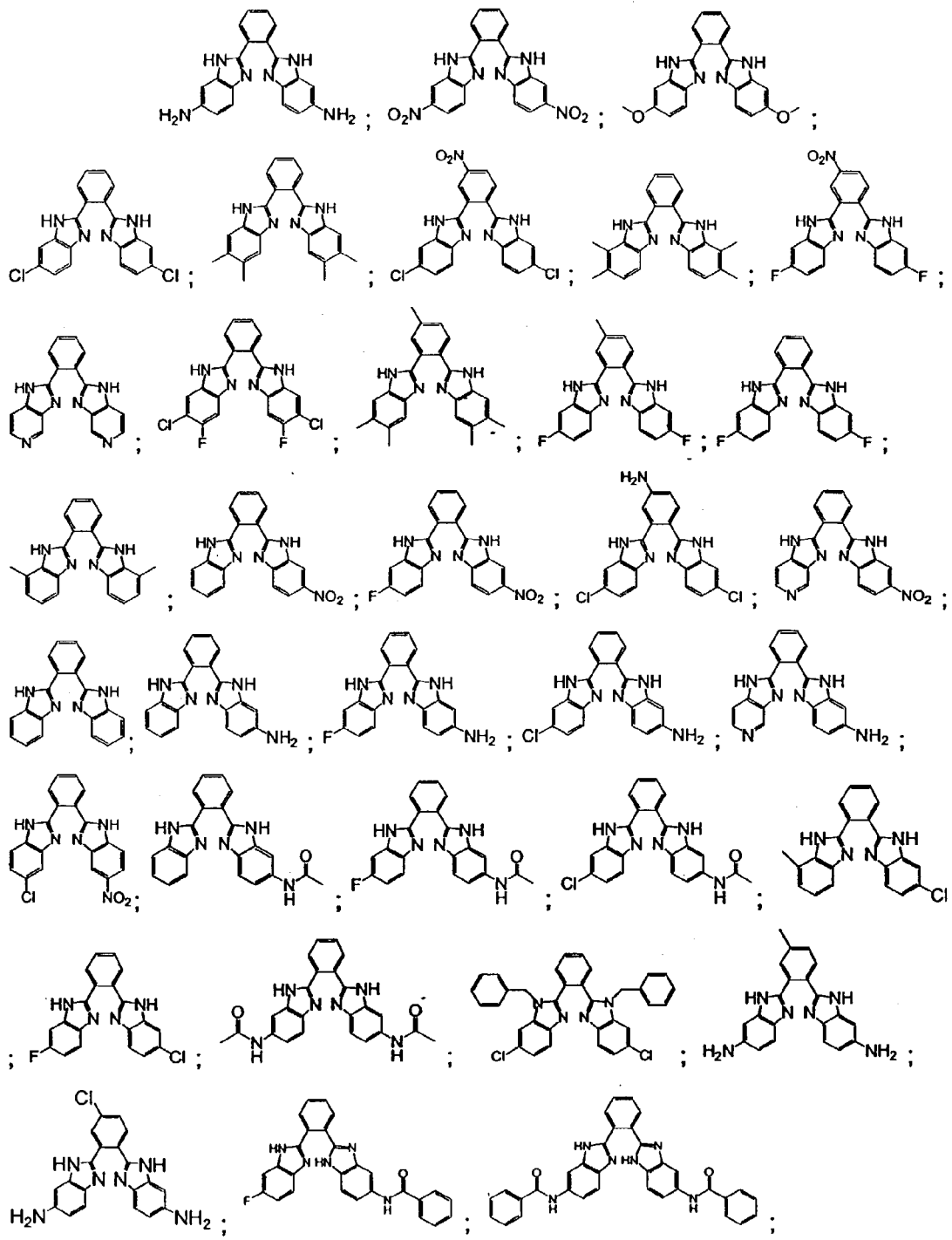
FIG. 1 displays structures of representative compounds of the invention.

Abbreviations and Definitions:

The abbreviations used herein have their conventional meaning within the scientific arts. For example: CHO, Chinese hamster ovary; EBSS, Earl's Balanced Salt Solution; hSK (or SK), $Ca^{2+}$ activated small conductance potassium channels; SDS, sodium dodecyl sulfate; $Et_3N$, triethylamine; MEOH, methanol; and DMSO, dimethylsulfoxide.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Compound of the invention," as used herein, is a compound according to Formula I, or a pharmaceutically acceptable salt of a compound according to Formula I.

"Modulating," as used herein, refers to the ability of a compound of the invention to activate and/or inhibit an SK potassium channel.

"Activating," as used herein, refers to the partial or full stimulation of an SK channel by a compound of the invention, which leads to an increase in ion flux either into or out of a cell in which an SK channel is found.

"Inhibiting" and "blocking," are used interchangeably herein to refer to the partial or full blockade of an SK channel by a compound of the invention, which leads to a decrease in ion flux either into or out of a cell in which an SK channel is found.

Where substituent groups are specified by their conventional chemical formulae, written from left to right, they equally encompass the chemically identical substituents which would result from writing the structure from right to left, e.g., —$CH_2O$— is intended to also recite —$OCH_2$—; —$NHS(O)_2$— is also intended to represent —$S(O)_2HN$—; etc.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N, S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

In general, an "acyl substituent" is also selected from the group set forth above. As used herein, the term "acyl substituent" refers to groups attached to, and fulfilling the valence of a carbonyl carbon that is either directly or indirectly attached to the polycyclic nucleus of the compounds of the present invention.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo ($C_1$–$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroalkyl substituents," respectively, and they can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1–3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, the aryl substituents and heteroaryl substituents are generally referred to as "aryl substituents" and "heteroaryl substituents," respectively and are varied and selected from, for example: halogen, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro($C_1$–$C_4$)alkoxy, and fluoro($C_1$–$C_4$)alkyl, in a number ranging from zero to the total number of open valences on the aromatic ring system; and where R', R", R''' and R'''' are preferably independently selected from hydrogen, ($C_1$–$C_8$)alkyl and heteroalkyl, unsubstituted aryl and heteroaryl, (unsubstituted aryl)-($C_1$–$C_4$)alkyl, and (unsubstituted aryl)oxy-($C_1$–$C_4$)alkyl. When a compound of the invention includes more than one R group, for example, each of the R groups is independently selected as are each R', R", R''' and R'''' groups when more than one of these groups is present.

Two of the aryl substituents on adjacent atoms of the aryl or heteroaryl ring may optionally be replaced with a substituent of the formula —T—C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$–C$_6$)alkyl.

The term "alkyl amide" refers to carboxylic acid amides that are functionalized on the amide nitrogen by one or more alkyl groups as defined herein.

The term "alkyl amine" refers to amines in which the nitrogen atom is functionalized with one or more alkyl groups as defined herein.

As used herein, the term "heteroatom" includes oxygen (O), nitrogen (N), sulfur (S) and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Introduction

The development of therapeutic agents, which act on potassium ion channels has received considerable recent attention. Efforts to elucidate the structure of compounds active towards the SK family of ion channels have led to the discovery of diverse species. For example, a family of N-alkyl benzamides that act by inhibiting potassium channels has been described (see, PCT/US98/02364, published as WO 98/37068). Teuber and coworkers have also described a genus of compounds active towards SK channels in which two benzimidazole groups are connected through a linker arm, which is attached to an endocyclic amine moiety of the benzimidazole. The present invention provides a family of SK-active bis-benzimidazoles with a structure that is distinct from the above-referenced genera.

The present invention provides compounds, compositions, and methods for decreasing ion flux in voltage-dependent potassium channels, particularly the channels of the small conductance, calcium activated potassium channels (e.g., hSK1, hSK2, and hSK3). The SK family of channels is implicated in a number of disorders that are targets for a therapeutic or prophylactic regimen, which functions by modulating one or more members of the SK channel family. The compounds of the present invention are useful to treat central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, psychosis, anxiety, depression, dementia, memory and attention deficits, Alzheimer's disease, age-related memory loss, learning deficiencies, anxiety, traumatic brain injury, dysmenorrhea, narcolepsy and motor neuron diseases), as well as active as neuroprotective agents (e.g., to prevent stroke and the like). The compounds of the invention are also useful in treating disease states such as gastroesophogeal reflux disorder and gastrointestinal hypomotility disorders, irritable bowel syndrome, secretory diarrhea, asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, ischemia, cerebral ischemia, ischemic heart disease, angina pectoris, coronary heart disease, Reynaud's disease, intermittent claudication, Sjorgren's syndrome, arrhythmia, hypertension, myotonic muscle dystrophia, xerostomi, diabetes type II, hyperinsulinemia, premature labor, baldness, cancer, and immune suppression.

The compounds provided herein are shown to act as potassium channel modulators, particularly for members of the SK family of ion channels (e.g., hSK1, hSK2, and hSK3).

DESCRIPTION OF THE EMBODIMENTS

I. Modulators of Voltage-Dependent Potassium Channels

In one aspect, the present invention provides compounds having a structure according to Formula I:

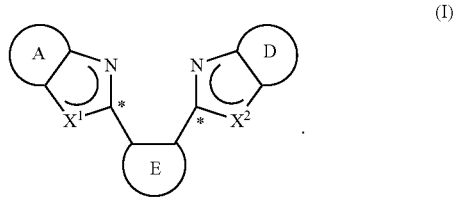

(I)

In Formula I, ring systems A, D and E are independently selected from substituted or unsubstituted aryl, and substituted or unsubstituted heteroaryl ring systems. The symbols $X^1$ and $X^2$ independently represent $NR^1$, S, O, $NHC(R^2)$, $SC(R^3)$, $OC(R^4)$, and $C(R^5)$. $R^1$, $R^2$, $R^3$, $R^4$, and $R^5$ independently represent H and substituted or unsubstituted alkyl, substituted or unsubstituted arylalkyl and substituted or unsubstituted heteroaryl. The semicircular bond within the heterocyclic ring system indicates that a double bond may be located between the carbon marked * and N or this carbon and $X^1$ or, alternatively $X^2$.

In an exemplary embodiment, the invention provides a compound in which the ring systems A, D and E are independently selected from substituted or unsubstituted phenyl and substituted or unsubstituted pyridyl ring systems.

In another exemplary embodiment, the invention provides a compound in which the substituted phenyl ring systems, A and D, are substituted with a member selected from $NH_2$, alkyl amines, aryl amines, carboxyl, esters, $C(O)NH_2$, alkyl amides, aryl amides, sulfonamides, thioureas, halogens, alkoxy, carbamate, ether, hydroxy, imides and combinations thereof.

The activity of the compounds of the invention towards ion channels of the SK family is readily assayed by those of skill using methods known in the art, including that set forth in Example 11.

Representative compounds according to Formula I and their activities are displayed in Table 1.

| Structure | Analytical Data [M + 1]⁺ | Activity |
|---|---|---|
| 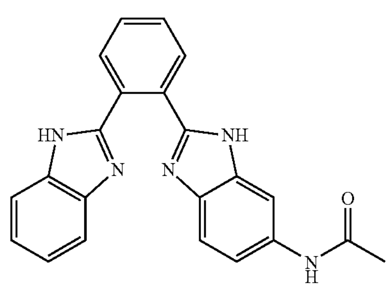 | 368 | +++ |
| 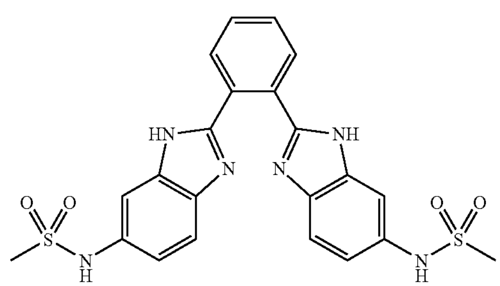 | 497 | +++ |

-continued

| Structure | Analytical Data [M + 1]⁺ | Activity |
|---|---|---|
| 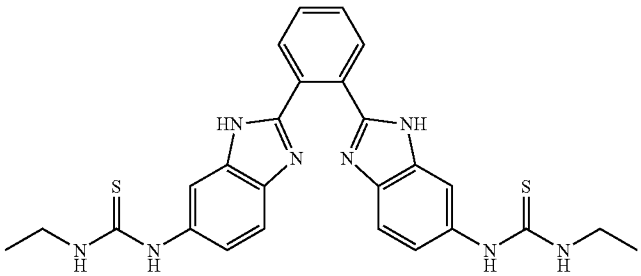 | 515 | +++ |
| 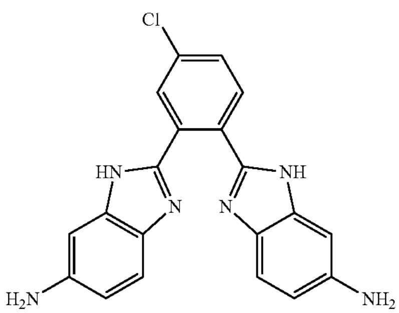 | 375 | ++ |
| 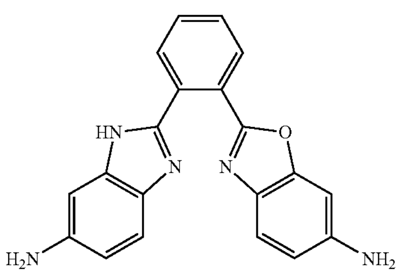 | 342 | + |
| 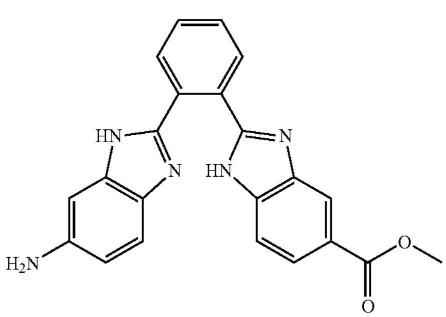 | 386 | + |

Figure 1B:
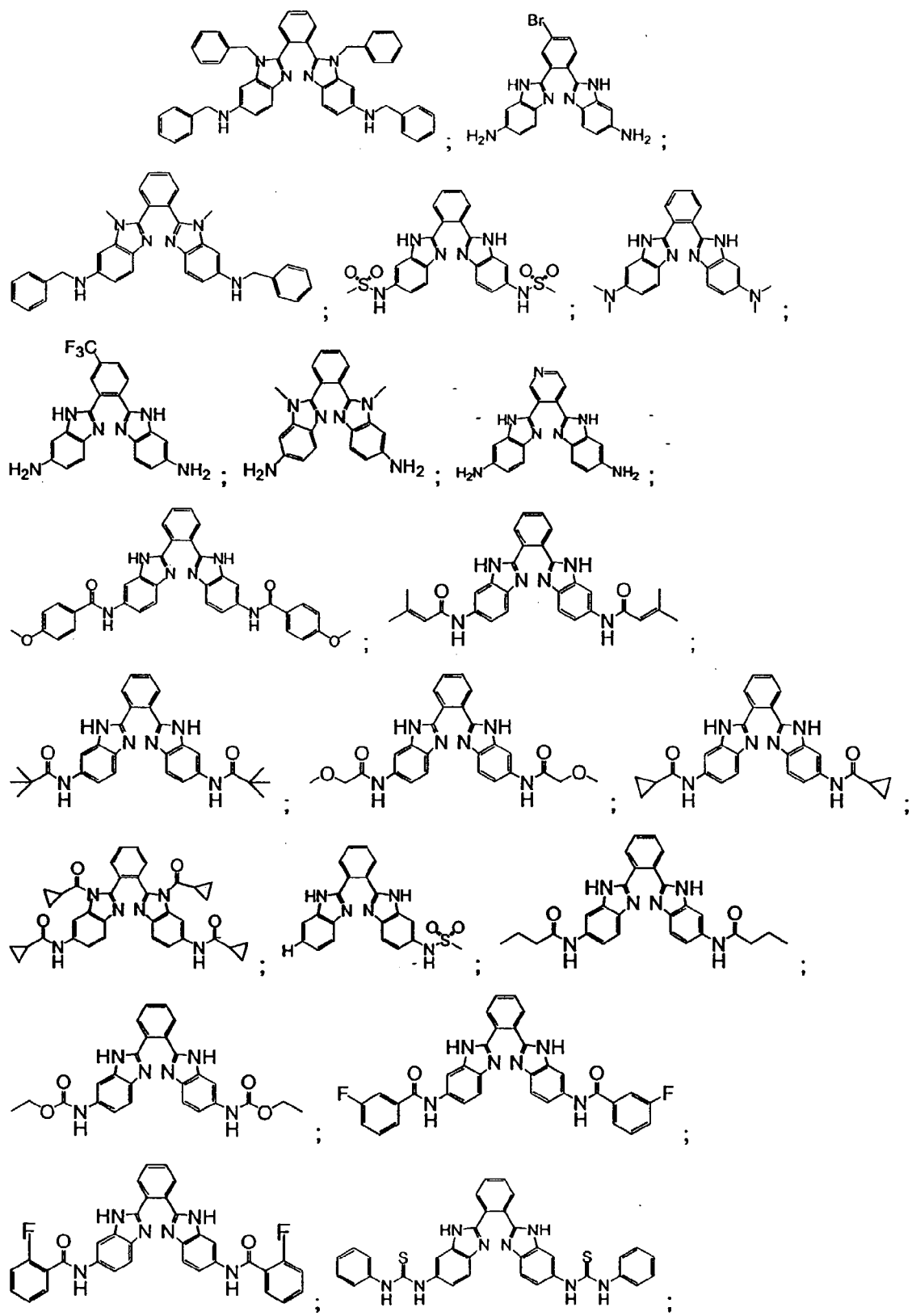
Figure 1C:
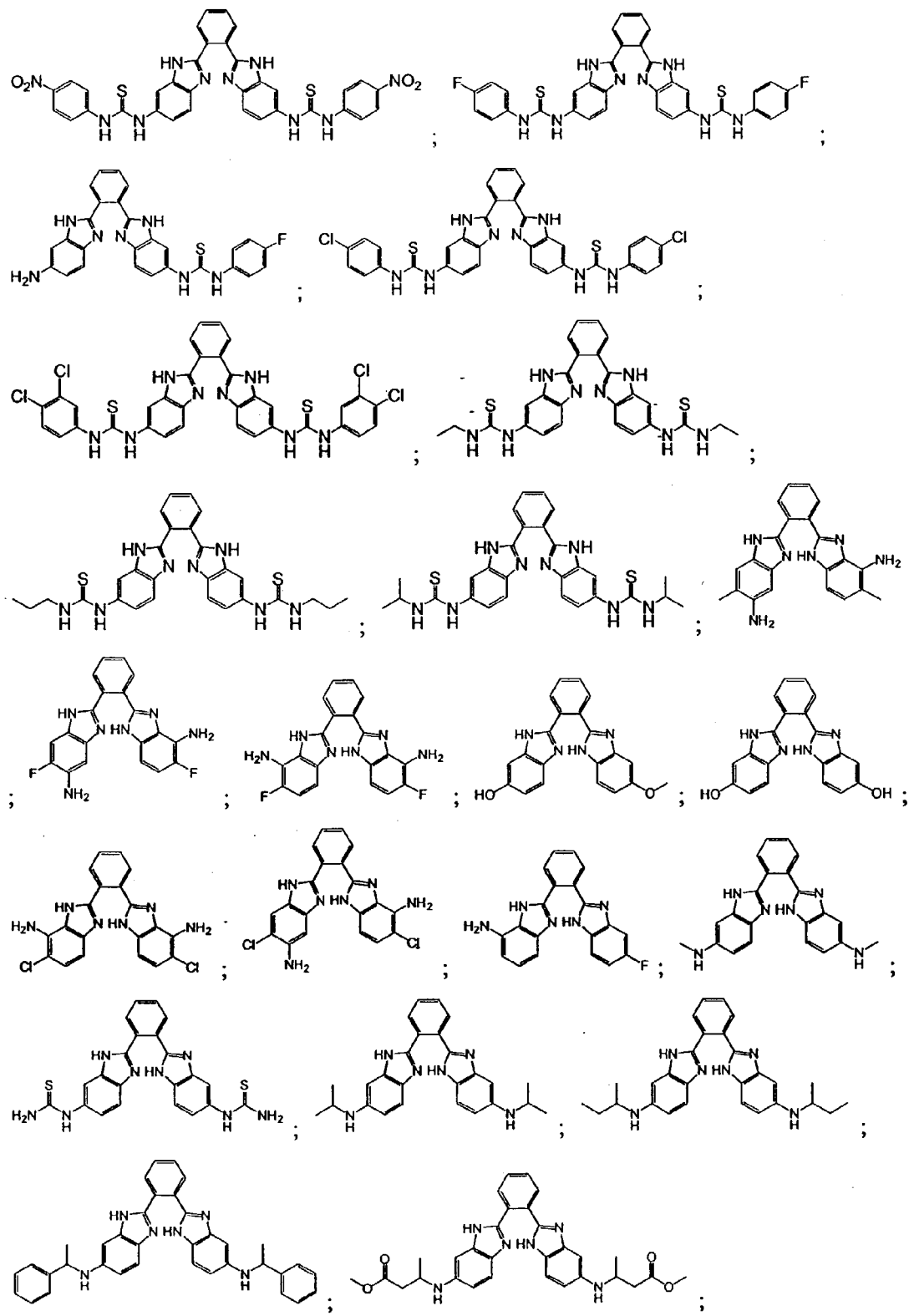
Figure 1D:
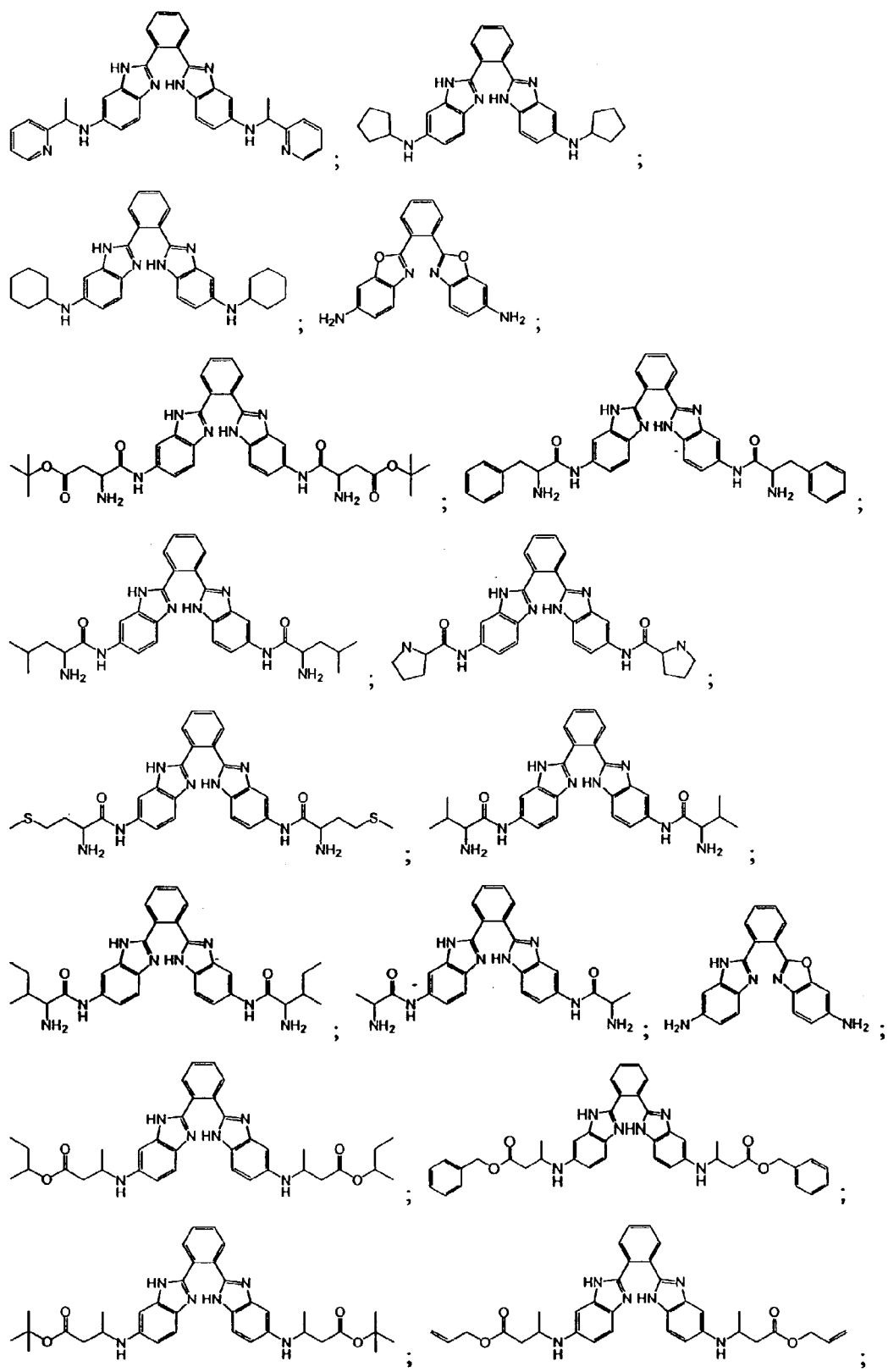
Figure 1E:
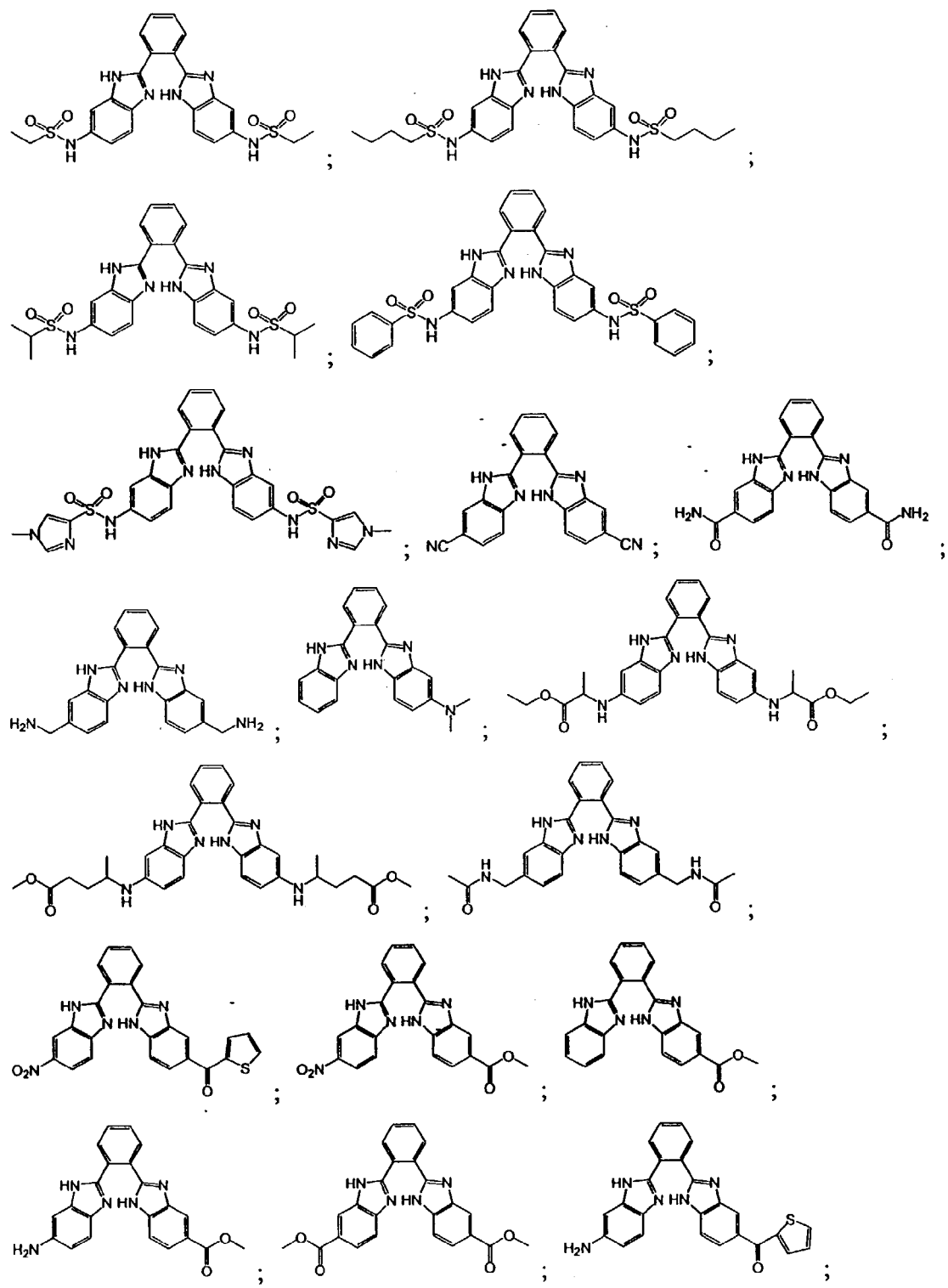
Figure 1F:
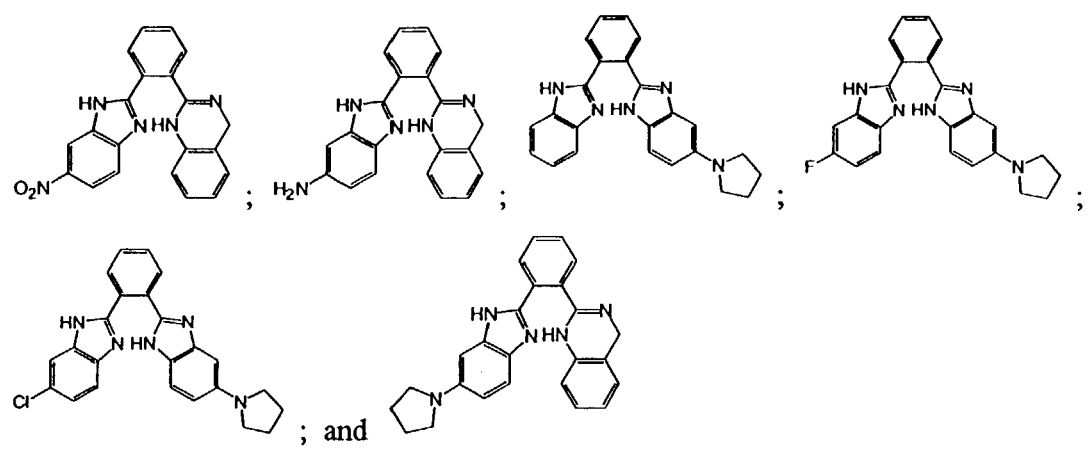

These and other exemplary compounds of the invention are set forth in FIG. 1.

Also provided by the present invention are compounds having a structure according to Formula II:

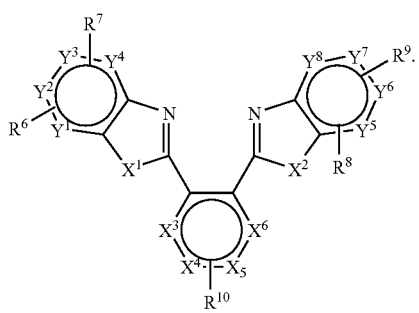

(II)

In Formula II, the symbols $X^3$, $X^4$, $X^1$, $X^6$, $Y^1$, $Y^2$, $Y^3$, $Y^4$, $Y^5$, $Y^6$, $Y^7$, and $Y^8$ represent members independently selected from $C(R^{11})$ and N, with the proviso that no more than two of $Y^1$, $Y^2$, $Y^3$, and $Y^4$ are N, and no more than two of $Y^5$, $Y^6$, $Y^7$, and $Y^8$ are N. $R^6$, $R^7$, $R^8$, $R^9$, and $R^{11}$ represent members independently selected from H, $NH_2$, alkyl amines, aryl amines, carboxyl, $C(O)NH_2$, alkyl amides, aryl amides, sulfonamides, thioureas, esters, halogens, alkoxy, carbamate, ether, hydroxy, substituted or unsubstituted alkyl, ketone and combinations thereof. $R^6$ and $R^7$ are optionally joined to form a ring, and $R^8$ and $R^9$ are optionally joined to form a ring. The symbol $R^{10}$ represents H, OH, $NH_2$, halogen, substituted or unsubstituted alkyl, substituted or unsubstituted aryl, substituted or unsubstituted heteroaryl, substituted or unsubstituted heterocycloalkyl, and substituted or unsubstituted arylalkyl groups.

For each of the compounds of the present invention, when two or more substituents of a compound of the invention are joined to form a ring, the ring is preferably a heterocyclic ring, which can be saturated, or have one or more degrees of unsaturation. Moreover, the ring itself can bear substituents such as those disclosed herein as appropriate for alkyl and aryl groups. Representative ring structures include cyclic imides, cyclic lactams, cyclic ureas, and cyclic carbamates. Exemplary rings have from four to eight members, from four to six members and five to six members.

Further compounds provided by the present invention include those according to Formula III:

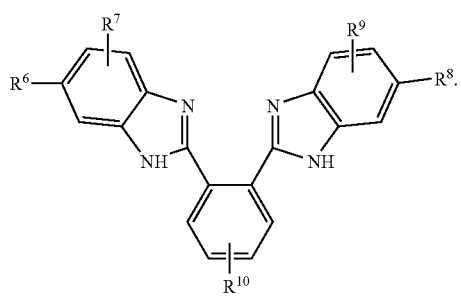

(III)

In Formula III, the symbols $R^6$, $R^7$, $R^8$, and $R^9$ independently represent halogen, substituted or unsubstituted alkyl, $C(O)R^{12}$ or $NR^{13}R^{14}$, with the proviso that no more than one of $R^6$ and $R^7$ is H and if one of $R^6$ and $R^7$ is $NH_2$, neither $R^8$ nor $R^9$ is $NH_2$. The symbol $R^{12}$ represents H, substituted or unsubstituted alkyl, $OR^8$, or $NR^9R^{20}$. $R^{18}$, $R^{19}$ and $R^{20}$ independently represent H or substituted or unsubstituted alkyl. $R^{19}$ and $R^{20}$ together with the nitrogen to which they are attached are optionally joined to form a ring. The symbols $R^{13}$ and $R^{14}$ together with the nitrogen to which they are bound are optionally joined together into a ring and independently represent H, substituted or unsubstituted alkyl, $C(O)NR^{15}R^{16}$, $C(S)NR^{15}R^{16}$, $S(O)_2R^{17}$, $C(O)R^{17}$, or $C(O)R^{17}$. $R^{15}$ and $R^{16}$ are members independently selected from the group consisting of H, substituted or unsubstituted alkyl, substituted or unsubstituted heteroalkyl, substituted or unsubstituted aryl and substituted or unsubstituted heteroaryl, and together with the nitrogen to which they are attached are optionally joined into a ring. $R^{17}$ represents substituted or unsubstituted alkyl, substituted or unsubstituted heteroalkyl, substituted or unsubstituted aryl or substituted or unsubstituted heteroaryl. The symbol $R^{10}$ represents H, OH, $NH_2$, halogen or substituted or unsubstituted alkyl groups.

In an exemplary embodiment, $R^5$, $R^6$, $R^7$, and $R^8$ are independently selected from H, $NH_2$, substituted or unsubstituted alkyl, substituted or unsubstituted aryl, substituted or unsubstituted heteroaryl, $NHC(O)O(C_1-C_{10})$alkyl, $NHC(O)-(C_1-C_{10})$alkyl; halogen; $NHS(O)_2-(C_1-C_{10})$alkyl; and $NHC(S)NH-(C_1-C_{10})$alkyl, with the proviso that $R^5$ and $R^7$ are not both H. In each of the exemplary functional groups set forth above, $(C_1-C_{10})$alkyl includes both substituted and unsubstituted alkyl groups.

Exemplary $(C_1-C_{10})$alkyl groups include, for example, $-CH_3$; $-CH_2CH_3$; $-CH_2CH_2CH_3$; i-Pr; $-CH_2(CH_3)CH_3$; $-CH_2(CH_3)CH_3$; $-CH_2=CH_3$; $-_{CH2}=(CH_3)_2$; $-OCH_3$; $-CH(CH_3)_3$; cyclopropyl. Exemplary substituted alkyl groups include, $-CH_2(CH_3)$-pyridyl; $-((C_1-C_{10})$alkyl)-$C(O)O-((C_1-C_{10})$alkyl); $-((C_1-C_{10})$alkyl)-aryl; and $-((C_1-C_{10})$alkyl)-heteroaryl.

In other exemplary embodiments, the $(C_1-C_{10})$alkyl groups are replaced by aryl or heteroaryl groups, including, but not limited to substituted or unsubstituted phenyl; substituted or unsubstituted thienyl, and the like.

Also within the scope of the present invention are compounds of the invention that are poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, is attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Moreover, the present invention includes compounds within the motif set forth in Formulae I and II, which are functionalized to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to, for example, replace a hydroxyl group with a diol, or an amine with a quaternary amine, hydroxy amine or similar more water-soluble moiety. In a preferred embodiment, additional water solubility is imparted by substitution at a site not essential for the activity towards the ion channel of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

Preparation of Potassium Channel Modulators

Compounds of the present invention can be prepared using readily available starting materials or known intermediates. Scheme 1 sets forth an exemplary synthetic scheme for the preparation of compounds of the invention.

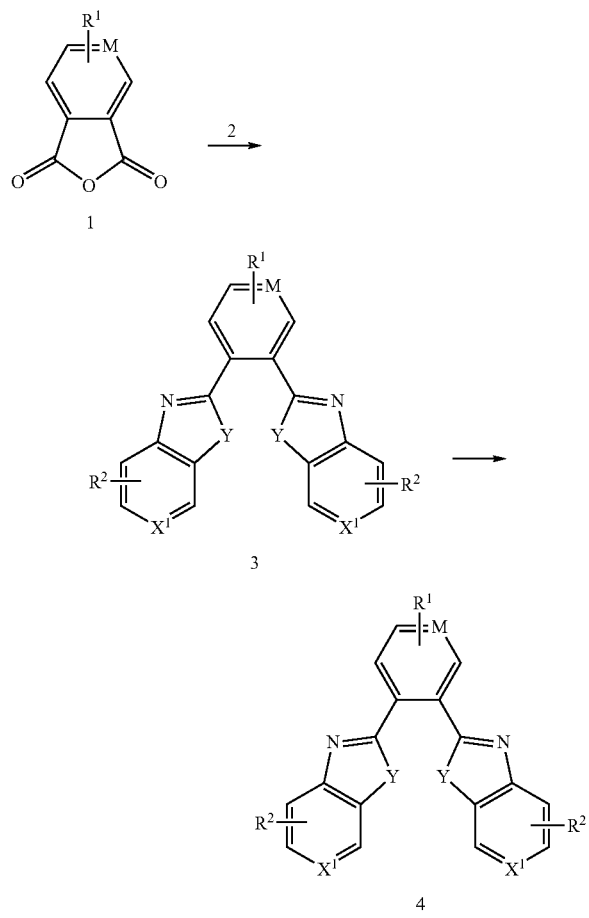

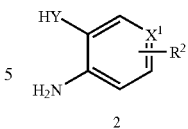

-continued

In Scheme I, the symbols M and $X^1$ independently represent CH or N. $R^1$ and $R^2$ are substantially as described above. YH is a member selected from OH, SH and $NH_2$.

In an exemplary process, compound 3 is assembled by contacting anhydride 1 with amine 2 in the presence of acetic acid. In another embodiment, compounds 1 and 2 are treated with polyphosphoric acid to produce compound 3. In a still further embodiment, compound 3 is synthesized by adsorbing the reactants 1 and 2 onto silica gel and submitting the resulting mixture to microwaves, e.g., in a household microwave oven.

Compound 3 is converted to compound 4 by one of an array of routes. In an exemplary preparation, compound 3 is treated with Pd/C under an atmosphere of $H_2$.

After assembly of the tricyclic ring system, the individual rings can be elaborated by any art-recognized means. A number of exemplary elaboration schemes are set forth in the Examples appended hereto.

Methods for preparing dimers, trimers and higher homologs of small organic molecules, such as those of the present invention, as well as methods of functionalizing a polyfunctional framework molecule are well known to those of skill in the art. For example, an aromatic amine of the invention is converted to the corresponding isothiocyanate by the action of thiophosgene. The resulting isothiocyanate is coupled to an amine of the invention, thereby forming either a homo- or heterodimeric species. Alternatively, the isothiocyanate is coupled with an amine-containing backbone, such as polylysine, thereby forming a conjugate between a polyvalent framework and a compound of the invention. If it is desired to prepare a heterofunctionalized polyvalent species, the polylysine is underlabeled with the first isothiocyanate and subsequently labeled with one or more different isothiocyanates. Alternatively, a mixture of isothiocyanates is added to the backbone. Purification proceeds by, for example, size exclusion chromatography, dialysis, nanofiltration and the like.

II. Assays for Modulators of Potassium Ion Channels

SK monomers as well as SK alleles and polymorphic variants are subunits of potassium channels. The activity of a potassium channel comprising SK subunits can be assessed using a variety of in vitro and in vivo assays, e.g., measuring current, measuring membrane potential, measuring ion flux, e.g., potassium or rubidium, measuring potassium concentration, measuring second messengers and transcription levels, using potassium-dependent yeast growth assays, and using e.g., voltage-sensitive dyes, radioactive tracers, and patch-clamp electrophysiology.

Furthermore, such assays can be used to test for inhibitors and activators of channels comprising SK. The SK family of channels is implicated in a number of disorders that are targets for a therapeutic or prophylactic regimen, which functions by modulating one or more members of the SK channel family. The compounds and methods of the invention are useful to treat central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, psychosis, anxiety, depression, dementia, memory and attention deficits, Alzheimer's disease, age-related memory loss, learning deficiencies, anxiety, traumatic brain injury, dysmenorrhea, narcolepsy and motor neuron diseases), as well as active as neuroprotective agents (e.g., to prevent stroke and the like). The compounds of the invention are also useful in treating disease states such as gastroesophogeal reflux disorder and gastrointestinal hypomotility disorders, irritable bowel syndrome, secretory diarrhea, asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, ischemia, cerebral ischemia, ischemic heart disease, angina pectoris, coronary heart disease, Reynaud's disease, intermittent claudication, Sjorgren's syndrome, arrhythmia, hypertension, myotonic muscle dystrophia, xerostomi, diabetes type II, hyperinsulinemia, premature labor, baldness, cancer, and immune suppression.

Modulators of the potassium channels are tested using biologically active SK, either recombinant or naturally occurring, or by using native cells, like cells from the nervous system expressing an SK channel. SK channels can be isolated, co-expressed or expressed in a cell, or expressed in a membrane derived from a cell. In such assays, SK is expressed alone to form a homomeric potassium channel or is co-expressed with a second subunit (e.g., another SK family member) so as to form a heteromeric potassium channel. Modulation is tested using one of the in vitro or in vivo assays described above. Samples or assays that are treated with a potential potassium channel inhibitor or activator are compared to control samples without the test compound, to examine the extent of modulation. Control samples (untreated with activators or inhibitors) are assigned a relative potassium channel activity value of 100. Inhibition of channels comprising SK is achieved when the potassium channel activity value relative to the control is less than 70%, preferably less than 40% and still more preferably, less than 30%. Compounds that decrease the flux of ions will cause a detectable decrease in the ion current density by decreasing the probability of a channel comprising SK being open, by decreasing conductance through the channel, and decreasing the number or expression of channels.

Changes in ion flux may be assessed by determining changes in polarization (i.e., electrical potential) of the cell or membrane expressing the potassium channel. A preferred means to determine changes in cellular polarization is by measuring changes in current or voltage with the voltage-clamp and patch-clamp techniques, using the "cell-attached" mode, the "inside-out" mode, the "outside-out" mode, the "perforated cell" mode, the "one or two electrode" mode, or the "whole cell" mode (see, e.g., Ackerman et al., *New Engl. J. Med.* 336: 1575–1595 (1997)). Whole cell currents are conveniently determined using the standard methodology (see, e.g., Hamil et al., *Pflugers. Archiv.* 391: 85 (1981)). Other known assays include: radiolabeled rubidium flux assays and fluorescence assays using voltage-sensitive dyes (see, e.g., Vestergarrd-Bogind et al., *J. Membrane Biol.* 88: 67–75 (1988); Daniel et al., *J. Pharmacol. Meth.* 25: 185–193 (1991); Holevinsky et al., *J. Membrane Biology* 137: 59–70 (1994)). Assays for compounds capable of inhibiting or increasing potassium flux through the channel proteins can be performed by application of the compounds to a bath solution in contact with and comprising cells having a channel of the present invention (see, e.g., Blatz et al., *Nature* 323: 718–720 (1986); Park, *J. Physiol.* 481: 555–570 (1994)). Generally, the compounds to be tested are present in the range from about 1 pM to about 100 mM, preferably from about 1 pM to about 1 µM.

The effects of the test compounds upon the function of the channels can be measured by changes in the electrical currents or ionic flux or by the consequences of changes in currents and flux. Changes in electrical current or ionic flux are measured by either increases or decreases in the flux of ions such as potassium or rubidium ions. The cations can be measured in a variety of standard ways. They can be measured directly by concentration changes of the ions or indirectly by membrane potential or by radio-labeling of the ions. Consequences of the test compound on ion flux can be quite varied. Accordingly, any suitable physiological change can be used to assess the influence of a test compound on the channels of this invention. The effects of a test compound can be measured by a toxin-binding assay. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as $Ca^{2+}$, or cyclic nucleotides.

III. Pharmaceutical Compositions of Potassium Channel Modulators

In another aspect, the present invention provides pharmaceutical compositions comprising a pharmaceutically acceptable excipient and a compound of Formula I provided above.

Formulation of the Compounds (Compositions)

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of Formula I, or a pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

IV. Methods for Modulating Ion Flow in Voltage-Dependent Potassium Channels

In yet another aspect, the present invention provides methods for decreasing ion flow through voltage dependent potassium channels in a cell, comprising contacting a cell containing the target ion channels with a potassium channel-modulating amount of a compound of Formula I provided above.

The methods provided in this aspect of the invention are useful for the diagnosis of conditions that can be treated by modulating ion flux through voltage-dependent potassium channels, or for determining if a patient will be responsive to therapeutic agents, which act by modulating potassium channels. In particular, a patient's cell sample can be obtained and contacted with a compound of Formula I above and the ion flux can be measured relative to a cell's ion flux in the absence of a compound of Formula I. A decrease in ion flux will typically indicate that the patient will be responsive to a therapeutic regimen of ion channel modulators.

V. Methods for Treating Conditions Mediated by Voltage-Dependent Potassium Channels In still another aspect, the present invention provides a method for the treatment of a disorder or condition through modulation of a voltage-dependent potassium channel. In this method, a subject in need of such treatment is administered an effective amount of a compound having a structure according to Formula I. In a preferred embodiment, the compounds provided herein are used to treat a disorder or condition by modulating an ion channel of the hSK family.

The compounds provided herein are useful as potassium channel modulators and find therapeutic utility via modulation of voltage-dependent potassium channels in the treatment of diseases or conditions. The potassium channels that are typically modulated are described herein as voltage-dependent potassium channels such as the hSK potassium channels. As noted above, these channels may hSK1, hSK2, hSK3 and other members of the hSK family of ion channels.

The conditions that can be treated with the compounds and compositions of the present invention may include, but are not limited to, central or peripheral nervous system disorders (e.g., migraine, ataxia, Parkinson's disease, bipolar disorders, trigeminal neuralgia, spasticity, mood disorders, brain tumors, psychotic disorders, myokymia, seizures, epilepsy, hearing and vision loss, psychosis, anxiety, depression, dementia, memory and attention deficits, Alzheimer's disease, age-related memory loss, learning deficiencies, anxiety, traumatic brain injury, dysmenorrhea, narcolepsy and motor neuron diseases), as well as active as neuroprotective agents (e.g., to prevent stroke and the like). The compounds of the invention are also useful in treating disease states such as gastroesophogeal reflux disorder and gastrointestinal hypomotility disorders, irritable bowel syndrome, secretory diarrhea, asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, ischemia, cerebral ischemia, ischemic heart disease, angina pectoris, coronary heart disease, Reynaud's disease, intermittent claudication, Sjorgren's syndrome, arrhythmia, hypertension, myotonic muscle dystrophia, xerostomi, diabetes type II, hyperinsulinemia, premature labor, baldness, cancer, and immune suppression.

In treatment of the above conditions, the compounds utilized in the method of the invention are administered at the initial dosage of about 0.001 mg/kg to about 1000 mg/kg daily. A daily dose range of about 0.1 mg/kg to about 100 mg/kg is more typical. The dosages, however, may be varied depending upon the requirements of the patient, the severity of the condition being treated, and the compound being employed. Determination of the proper dosage for a par ticular situation is within the skill of the practitioner. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

EXAMPLES

The following examples are offered to illustrate, but not to limit the claimed invention.

In the examples below, unless otherwise stated, temperatures are given in degrees Celsius (° C.); operations were carried out at room or ambient temperature (typically a range of from about 18–25° C.; evaporation of solvent was carried out using a rotary evaporator under reduced pressure (typically, 4.5–30 mm Hg) with a bath temperature of up to 60° C.; the course of reactions was typically followed by TLC and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), LC-MS (liquid chromatography-mass spectrometry) and h (hours). The compounds of the invention were generally isolated in yields of from about 30% to about 90% using the methods set forth hereinbelow.

Unless otherwise specified, all solvents (HPLC grade) and reagents were purchased from suppliers and used without further purification. Reactions were conducted under a blanket of argon unless otherwise stated. Analytical TLC was performed on Whatman Inc. 60 silica gel plates (0.25 mm thickness). Compounds were visualized under a UV lamp (254 nM) or by developing with $KMnO_4$/KOH, ninhydrin or Hanessian's solution. Flash chromatography was done using silica gel from Selectro Scientific (particle size 32–63). $^1$H NMR, $^{19}$F NMR and $^{13}$C NMR spectra were recorded on a Varian 300 machine at 300 MHz, 282 MHz and 75.7 MHz, respectively. Melting points were recorded on a Electrothermal IA9100 apparatus and were uncorrected.

Example 1

Example 1 sets forth general procedures for the compounds of the invention in which the heteroatoms of the five-membered ring are either the same or different. The general method is understood by reference to Scheme 2, in which the preparation of an aniline derivative of the invention is exemplified.

Scheme 2

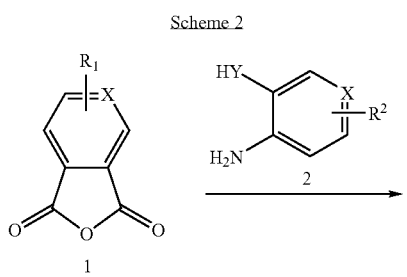

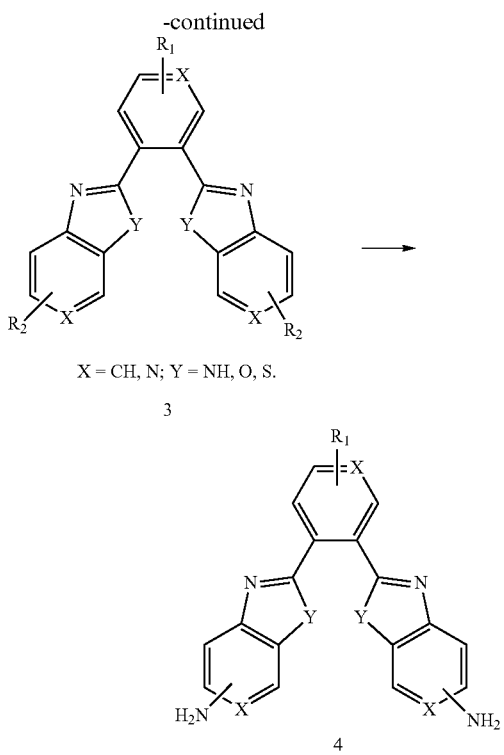

X = CH, N; Y = NH, O, S.

1.1 Coupling in Acetic Acid

A mixture of 1.0 mmol of anhydride 1 and 2.0 mmol of 2 in 100 mL of acetic acid was refluxed for two hours. When the reaction had cooled to room temperature, acetic acid was removed and the residue was purified either by column chromatography on silica gel or by recrystallization in ethyl acetate to give compound 3.

1.2 Coupling in Polyphosphoric Acid

A mixture of 1.35 mmol of anhydride 1 and 2.97 mmol of 2 in 1.5 mL of PPA was heated at 170° C. for four hours. The hot solution was then poured into saturated aqueous $NaHCO_3$. The mixture was then extracted 3 times with ethyl acetate. The combined organic layers were washed with saturated aqueous $NaHCO_3$ and then dried with $MgSO_4$. The ethyl acetate was removed in vacuo and the residue was purified by recrystallization in ethyl acetate to give compound 3.

1.3 Microwave Assisted Coupling

A mixture of 20.0 mmol of 2 and 10.0 mmol of anhydride 1 in 60 mL of DMF in a dish was stirred for 10 min at 80° C. Two hundred grams of silica gel was then added to the mixture. After the slurry was mixed well using a spatula, the mixture was irradiated in a household microwave oven (Emerson, model no. MW8778W, 1.2 kW) at energy level of 60 for 5 min. Then the solid mixture was stirred well with a spatula and put back into the microwave oven to irradiate for another 5 min. This process was repeated two more times (the reaction was monitored by LC-MS). After being cooled to room temperature, the silica gel mixture was filtered and washed with hot THF (10×200 mL) and MeOH (2×200 mL). The organic layers were combined and the solvent was removed to provide the crude product. Recrystallization of the crude product from THF/MeOH produced compound 3.

1.4 Results

Analytical results are provided below for exemplary embodiments of compound 3.

5-Nitro-2-[2-(5-nitro-1H-benzoimidazol-2-yl)-phenyl]-benzimidazole $^1$H NMR (300 MHz, DMSO-$d_6$) δ 13.5 (s, 2H), 8.40 (s, 2H), 8.02–8.10 (m, 4H), 7.78 (dd, $J_1$=3.3 Hz, $J_2$=5.8 Hz, 2H), 7.67 (d, $J_1$=8.8 Hz, 2H); MS m/z: 401 (M+1).

2-[2-(5,6-Dimethyl-1H-benzoimidazol-2-yl)-phenyl]-5,6-dimethyl-benzimidazole $^1$H NMR (300 MHz, DMSO-$d_6$) δ 8.08 (dd, $J_1$=3.3 Hz, $J_2$=5.8 Hz, 2H), 7.64 (dd, $J_1$=3.4 Hz, $J_2$=5.8 Hz, 2H), 7.38 (bs, 4H), 2.31 (s, 12H); MS m/z: 367 (M+1).

5-Methoxy-2-[2-(5-methoxy-1H-benzoimidazol-2-yl)-phenyl]-benzimidazole $^1$H NMR (300 MHz, CDCl$_3$) δ 7.75–7.71 (m, 2H), 7.65 (d, J=8.9 Hz, 2H), 7.19 (s, 2H), 7.00 (d, J=2.2 Hz, 2H), 6.94 (m, 2H), 3.93 (s, 6H); MS m/z: 371 (M+1).

1.5 Conversion of 3 to 4 via Hydrogenolysis

A mixture of 0.126 mmol of 3 and 45 mg of Pd/C (10%) in 5 mL of methanol was stirred for one hour under H$_2$ (1 atm). After filtering through celite, the solution was concentrated and the crude product was purified by column chromatography on silica gel to give compound 4.

1.6 Nickel(II) Mediated Conversion of 3 to 4

To a suspension of 18.8 mmol of compound 3 and 37.6 mmol of NiCl$_2$ in 1.0 L of a mixture of 400 mL of MeOH, 400 mL of THF, and 200 mL of saturated NH$_4$Cl was added excess NaBH$_4$ in portions over six hours. The reaction was monitored by LC-MS. When the reaction was complete, 15 mL of ethylenediamine was added and the resulting mixture was stirred for one hour before all solvents were removed. The residue was diluted with 300 mL MeOH and the inorganic solid was filtered and washed with MeOH (2×200 mL). After collecting all organic liquids and removing solvents, the crude product was purified by column chromatography over silica gel to give compound 4.

1.7 Results

Analytical results are provided below for exemplary embodiments of compound 4.

2-[4-(5-Amino-1H-benzoimidazol-2-yl)-pyridin-3-yl]-benzoimidazol-5-yl amine $^1$H NMR (300 MHz, CD$_3$OD) δ 9.15 (s, 2H), 8.70 (d, J=5.4 Hz, 2H), 8.05 (d, J=5.4 Hz, 2H), 7.44 (dd, $J_1$=3.4 Hz, $J_2$=8.5 Hz, 2H), 6.90 (d, J=10 Hz, 2H), 6.80 (d, J=8.7 Hz, 2H); MS m/z: 342 (M+1).

2-[2-(5-Chloro-1H-benzoimidazol-2-yl)-phenyl]-1H-benzoimidazol-5-yl amine $^1$H NMR (300 MHz, CD$_3$OD) δ 7.97 (dd, $J_1$=3.3 Hz, $J_2$=5.7 Hz, 2H), 7.74 (dd, $J_1$=3.3 Hz, $J_2$=5.8 Hz, 2H), 7.38 (d, J=8.7 Hz, 2H), 6.93 (s, 2H), 6.87 (d, J=8.5 Hz, 2H); MS m/z: 341 (M+1).

2-[2-(5-Amino-1H-benzoimidazol-2-yl)-phenyl]-1H-benzoimidazol-5-yl amine $^1$H NMR (300 MHz, CD$_3$OD) δ 7.97 (dd, $J_1$=3.3 Hz, $J_2$=5.7 Hz, 2H), 7.74 (dd, $J_1$=3.3 Hz, $J_2$=5.8 Hz, 2H), 7.38 (d, J=8.7 Hz, 2H), 6.93 (s, 2H), 6.87 (d, J=8.5 Hz, 2H); MS m/z: 341 (M+H).

Example 2

Example 2 sets forth an exemplary preparation of compounds of the invention in which the two heterocyclic rings do not have identical structures. The general method is exemplified in Scheme 3. Analytical results for exemplary compounds are provided.

Scheme 3

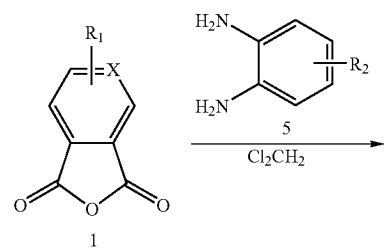

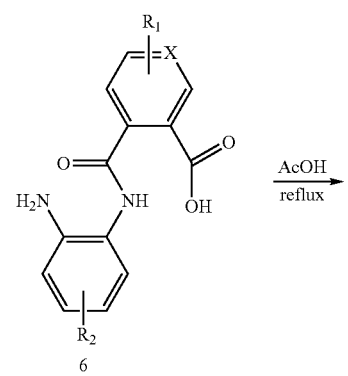

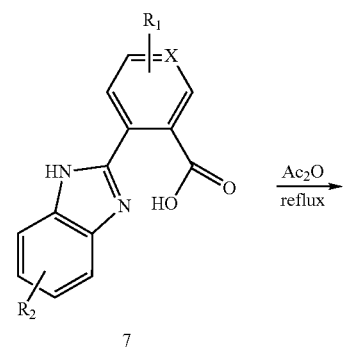

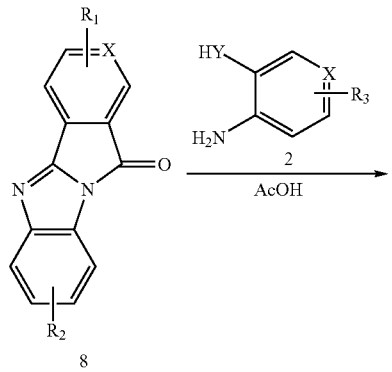

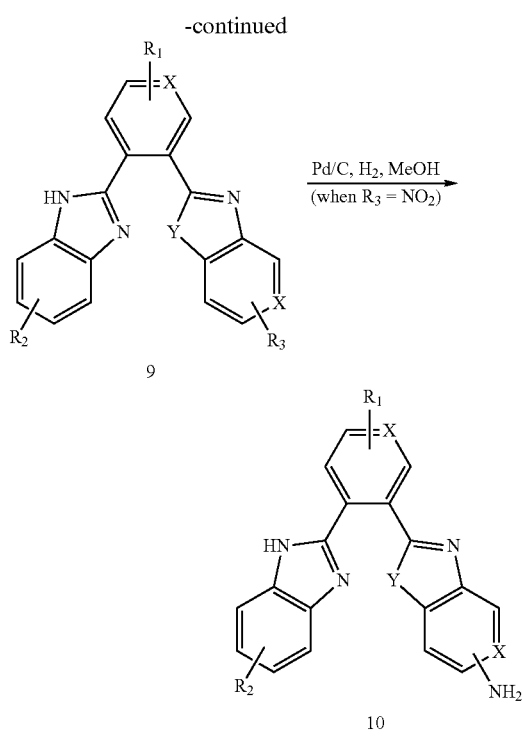

2.1 Preparation of 6 from 1

To a solution of 0.20 mol of anhydride 1 in 500 mL of dichloromethane was added a solution of 0.20 mol of 1,2-phenyl diamine 5 dropwise over two hours. The resulting mixture was stirred for between two hours and two days. A precipitate formed during this period. After filtration, the precipitate was further purified by triturating with ethyl acetate to give compound 6.

2.2 Results

Analytical results are provided below for an exemplary embodiment of compound 6.

N-(2-Amino-phenyl)-phthalamic acid $^1$H NMR (300 MHz, DMSO-$d_6$) δ 7.78 (dd, $J_1$=7.6 Hz, $J_2$=11.8 Hz, 2H), 7.66 (dd, $J_1$=7.3 Hz, $J_2$=14.8 Hz, 2H), 7.55–7.59 (m, 2H), 7.20 (dd, $J_1$=2.8 Hz, $J_2$=3.3 Hz, 2H); MS m/z: 257 (M+1).

2.3 Conversion of 6 to 7

A suspension or a solution of 10 mmol of 6 in 20 mL of acetic acid was refluxed for two hours during which time the mixture became clear. After the mixture was cooled to room temperature, acetic acid was removed in vacuo and the resulting solid was purified by trituration with a mixture of methanol and ethyl acetate to give compound 7.

2.4 Results

Analytical results are provided below for an exemplary embodiment of compound 7.

2-(1H-Benzoimidazol-2-yl)-benzoic acid $^1$H NMR (300 MHz, DMSO-$d_6$) δ 7.80–7.84 (m, 2H), 7.59–7.69 (m, 2H), 7.56 (dd, $J_1$=3.2 Hz, $J_2$=5.9 Hz, 2H), 7.20 (dd, $J_1$=3.1 Hz, $J_2$=5.9 Hz, 2H); MS m/z: 239 (M+1).

2.5 Conversion of 7 to 8

A suspension or a solution of 9.7 mmol of 7 in 20 mL of acetic anhydride was refluxed for two hours during which the mixture became clear. After cooling the mixture to room temperature, acetic anhydride was removed in vacuo and the resulting solid was used either without purification or after purification by trituration with a mixture of ethyl acetate and methanol.

2.6 Results

Analytical results are provided below for an exemplary embodiment of compound 8.

Benzo[4,5]imidazo[2,1-a]isoindol-11-one $^1$H NMR (300 MHz, DMSO-$d_6$) δ 7.85 (dd, $J_1$=3.9 Hz, $J_2$=7.5 Hz, 2H), 7.59–7.70 (m, 4H), 7.36 (dt, $J_1$=1.2 Hz, $J_2$=7.7 Hz, 1H), 7.28 (dt, $J_1$=1.4 Hz, $J_2$=7.9 Hz, 1H); MS m/z: 221 (M+1).

2.7 Conversion of 8 to 9

A mixture of 1.0 mmol of 8 and 1.0 mmol of 2 in 20 mL of acetic acid was refluxed for two hours. When the mixture was cooled to room temperature, acetic acid was removed and the residue was purified either by column chromatography on silica gel or by recrystallization in ethyl acetate to give compound 9.

2.8 Results

Analytical results are provided below for exemplary embodiments of compound 9.

5-Chloro-2-[2-(4-methyl-1H-benzoimidazol-2-yl)-phenyl]-benzothiazole $^1$H NMR (300 MHz, CD$_3$OD) δ 8.05–8.02 (m, 2H), 7.76–7.68 (m, 2H), 7.55–7.49 (m, 2H), 7.38–7.34 (m, 1H), 7.22 (dd, $J_1$=2 Hz, $J_2$=8.7 Hz, 1H), 7.13 (t, J=7.7 Hz, 1H), 7.03 (d, J=7.1 Hz, 1H), 2.54 (s, 3H); MS m/z: 359 (M+1).

2-[2-(1H-Benzoimidazol-2-yl)-phenyl]-5-nitro-benzimidazole $^1$H NMR (300 MHz, DMSO-$d_6$) δ 8.47 (s, 1H), 8.11–8.01 (m, 3H), 7.79–7.70 (m, 3H), 7.53 (s, 2H), 7.18 (dd, $J_1$=3.2 Hz, $J_2$=5.9 Hz, 2H); MS m/z: 356 (M+1).

2.9 Synthesis of 10 from 9

A mixture of 0.22 mmol of 9 and excess Pd/C (10%) in 20 mL methanol was stirred overnight under H$_2$ (1 atm). After filtering through celite, the solution was concentrated and the crude product was purified by column chromatography on silica gel to give a quantitative yield of 10.

2.10 Results

Analytical results are provided below for exemplary embodiments of compound 10.

2-[2-(1H-Benzoimidazol-2-yl)-phenyl]-1H-benzoimidazol-5-yl amine $^1$H NMR (300 MHz, DMSO-$d_6$) δ 8.20–8.16 (m, 1H), 8.04–8.00 (m, 1H), 7.67–7.59 (m, 4H), 7.34 (d, J=8.5 Hz, 1H), 7.18 (dd, $J_1$=3.1 Hz, $J_2$=6.1 Hz, 2H), 6.66 (s, 1H), 6.55 (d, J=8.5 Hz, 1H), 4.95 (bs, 2H); MS m/z: 326 (M+1).

2-[2-(5-Chloro-1H-benzoimidazol-2-yl)-phenyl]-1H-benzoimidazol-5-yl amine $^1$H NMR (300 MHz, DMSO-$d_6$) δ 8.25–8.10 (m, 1H), 7.97 (d, J=6.6 Hz, 1H), 7.70–7.61 (m, 4H), 7.20 (d, J=8.6 Hz, 2H), 6.70–6.60 (m, 1H), 6.55 (d, J=7.7 Hz, 1H); MS m/z: 360 (M+1).

Example 3

Example 3 sets forth a route by which the functional groups on the aromatic rings of the compounds can be further elaborated after assembly of the tricyclic nucleus. The functional group elaboration is exemplified by the conversion of an aniline amine group into the corresponding amide. The general method is understood by reference to Scheme 4. Analytical results are provided for exemplary compounds of the invention.

Scheme 4

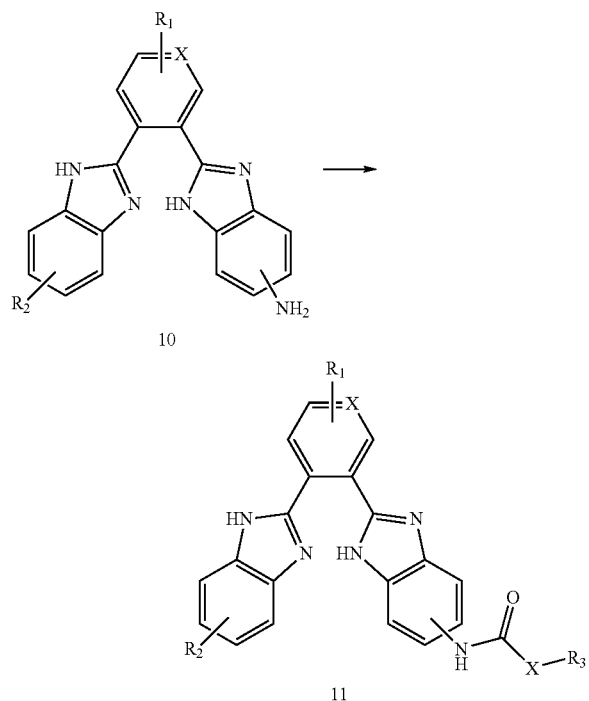

3.1 Conversion of 10 to 11 Using an Acid Chloride

A solution of 0.59 mmol of 10, 0.1 mL of triethylamine and 0.29 mmol of acid chloride in 3 mL of dichloromethane was stirred for twenty-four hours. The dichloromethane and excess acid chloride were removed under vacuum. The residue was dissolved in 3 mL of methanol followed by the addition of 10 mg of NaHCO$_3$. The resulting suspension was stirred from between four and fourteen hours before the solvent was removed in vacuo. The crude product was purified by column chromatography on silica gel to give compound 11.

3.2 Conversion of 10 to 11 Using an Anhydride

A solution of 3.69 mmol of 10 and 10 mL of acetic anhydride in 20 mL of pyridine was stirred for four hours. The pyridine and excess acetic anhydride were removed in vacuo. The residue was dissolved in 100 mL of methanol followed by the addition of 0.5 g of NaHCO$_3$. The resulting suspension was stirred from between four and fourteen hours before the solvent and the excess acetic anhydride were removed in vacuo. The crude product was purified by column chromatography on silica gel to give compound 11.

3.3 Conversion of 10 to 11 Using a Coupling Reagent

A solution of 0.059 mmol of 10, 0.05 mL triethylamine, 62 mg of BOP-reagent and 0.29 mmol in 4 mL of THF was shaken for twenty-four hours. LC-Mass analysis indicated that all starting material was consumed. The reaction mixture was concentrated in vacuo. The residue was dissolved in 4 mL of ethyl acetate and washed with sat. NaHCO$_3$. The residue was then concentrated in vacuo and dissolved in 0.5 mL of DMF. Piperidine (0.05 mL) was added and the mixture was shaken for one hour. After concentrating in vacuo the crude product was purified by reverse phase preparative column chromatography to give compound 11.

3.4 Results

Analytical data for exemplary compounds of structure 11 are provided below.

N-{2-[2-(5-Acetylamino-1H-benzoimidazol-2-yl)-phenyl]-1H-benzoimidazol-5-yl}-acetamide $^1$H NMR (300 MHz, DMSO-d$_6$) δ 7.94–7.90 (m, 4H), 7.65 (dd, J$_1$=3.4 Hz, J$_2$=5.5 Hz, 2H), 7.54–7.41 (m, 2H), 7.24–7.09 (m, 2H), 2.02 (s, 6H); MS m/z: 425 (M+1).

2-Amino-N-(2-{2-[5-(2-amino-propionylamino)-1H-benzoimidazol-2-yl]-phenyl}-1H-benzoimidazol-5-yl)-propionamide $^1$H NMR (300 MHz, CD$_3$OD) δ 8.19 (s, 2H), 8.09–8.05 (m, 2H), 7.89–7.86 (m, 2H), 7.59 (d, J=8.9 Hz, 2H), 7.43 (d, J=8.7 Hz, 2H), 4.09 (q, J=7.2 Hz, 2H), 1.62 (d, J=7.0 Hz, 6H); MS m/z: 483 (M+1).

N-{2-[2-(5-Butyrylamino-1H-benzoimidazol-2-yl)-phenyl]-1H-benzoimidazol-5-yl}-butyramide $^1$H NMR (300 MHz, DMSO-d$_6$) δ 8.07–7.95 (m, 4H), 7.66 (s, 3H), 7.55–7.45 (m, 1H), 7.45–7.25 (m, 1H), 7.15 (bs, 1H), 2.28 (t, J=7.2 Hz, 4H), 1.61 (q, J=7.5 Hz, 4H), 0.91 (t, J=7.3 Hz, 6H); MS m/z: 481 (M+1).

N-{2-[2-(5-Ethoxycarbonylamino-1H-benzoimidazol-2-yl)-phenyl]-1H-benzoimidazol-5-yl}-carbamic acid ethyl ester $^1$H NMR (300 MHz, CD$_3$OD) δ 7.98 (dd, J$_1$=3.5 Hz, J$_2$=5.7 Hz, 2H), 7.78 (s, 2H), 7.68 (dd, J$_1$=3.3 Hz, J$_2$=5.8 Hz, 2H), 7.46 (d, J=8.9 Hz, 2H), 7.17 (d, J=8.5 Hz, 2H), 4.19 (q, J=6.9 Hz, 4H), 1.31 (t, J=7.1 Hz, 6H); MS m/z: 481 (M+1).

N-{2-[2-(5-(4-methoxy-benzoylamino)-1H-benzoimidazol-2-yl)-phenyl]-1H-benzoimidazol-5-yl}-4-methoxy-benzamide $^1$H NMR (300 MHz, CD$_3$OD) δ 8.03 (s, 2H), 8.00 (dd, J$_1$=3.4 Hz, J$_2$=5.7 Hz, 2H), 7.92 (d, J=8.7 Hz, 4H), 7.69 (dd, J$_1$=3.4 Hz, J$_2$=5.7 Hz, 2H), 7.53 (d, J=8.7 Hz, 2H), 7.43 (d, J=8.7 Hz, 2H), 7.02 (d, J=8.9 Hz, 4H), 3.86 (s, 6H); MS m/z: 609 (M+1).

Example 4

Example 4 sets forth a procedure for the elaboration of an aniline amine substituent and its conversion to the corresponding sulfonamide. The method is exemplified by the conversion of compound 10 to sulfonamide 12. The general method is understood by reference to Scheme 5. Analytical data for representative compounds of structure 12 are provided.

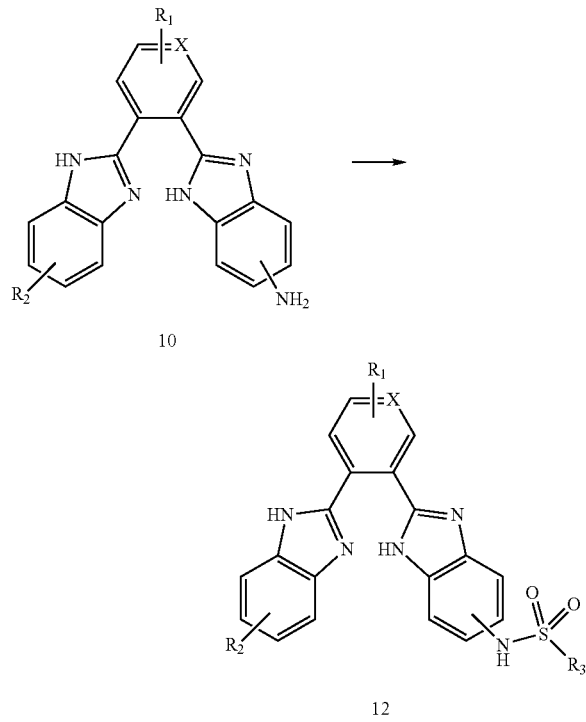

Scheme 5

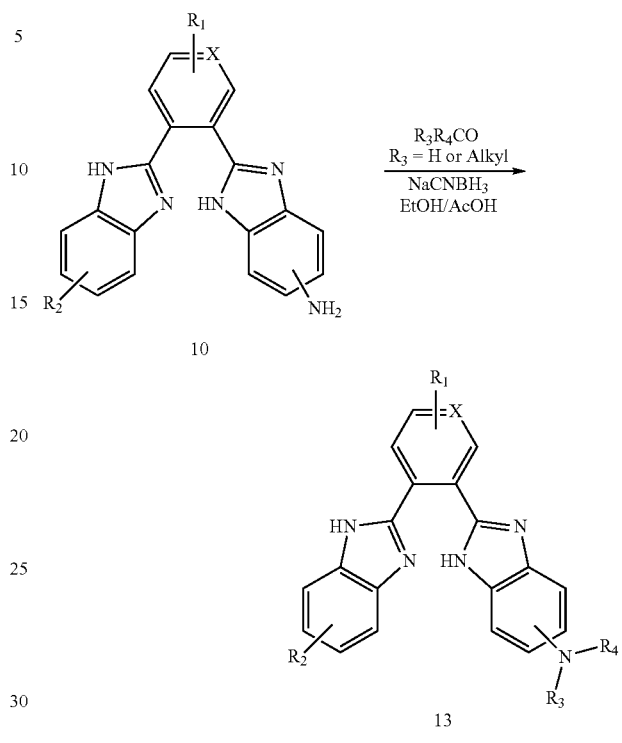

Scheme 6

5.1 Reductive Alkylation of 10 to Form 13

Sodium cyanoborohydride (0.44 mmol) was added to a solution of 0.044 mmol of 10 and 0.44 mmol of carbonyl compound in 2.5 mL of 4:1 ethanol/acetic acid. The solution was stirred for two hours and then the solvent was removed under vacuum. The residue was dissolved in ethyl acetate and the organic solution was washed with water. The organic layer was dried with magnesium sulfate. The crude product was concentrated in vacuo and purified by column chromatography on silica gel to give compound 13.

5.2 Results

Analytical data for exemplary compounds of structure 13 are provided below.

4.1 Sulfonylation of 10 to 12

A solution of 0.088 mmol of 10, 0.1 mL of pyridine and 0.194 mmol of sulfonyl chloride in 5 mL of acetonitrile was stirred for 2 days. Pyridine, acetonitrile, and excess sulfonyl chloride were removed under vacuum. The residue was dissolved in 5 mL of methanol and 0.5 mL of 6N NaOH was added. The resulting suspension was refluxed for a half hour, after which the pH of the mixture was made neutral with saturated $NH_4Cl$. The crude product was concentrated in vacuo and purified by column chromatography on silica gel to give compound 12.

4.2 Results

Analytical data for an exemplary compound of structure 12 are provided below.

N-{2-[2-(1H-Benzoimidazol-2-yl)-phenyl]-1H-benzoimidazol-5-yl}-methanesulfonamide $^1$H NMR (300 MHz, $CD_3OD$) δ 7.94 (bs, 2H), 7.66 (bs, 2H), 7.57–7.49 (m, 4H), 7.24 (d, $J_1$=3.1 Hz, $J_2$=6.1 Hz, 2H), 7.14 (d, J=8.7 Hz, 1H), 2.91 (s, 3H); MS m/z: 404 (M+1).

Example 5

Example 5 provides another method of elaborating the aniline amine groups of the compounds of the invention by either mono- or di-alkylating the amine moiety. The general method is understood by reference to Scheme 6. Analytical data is provided for exemplary compounds of structure 13.

{2-[2-(1H-(1-phenyl-ethylamino)-benzoimidazol-2-yl)-phenyl]-1H-benzoimidazol-5-yl}-(1-phenyl-ethyl)-amine $^1$H NMR (300 MHz, $CD_3OD$) δ 7.87–7.83 (m, 2H), 7.59 (dd, $J_1$=3.4 Hz, $J_2$=5.7 Hz, 2H), 7.37 (d, J=7.8 Hz, 4H), 7.29–7.22 (m, 6H), 7.18–7.12 (m, 2H), 6.74 (d, J=8.7 Hz, 2H), 6.44–6.41 (m, 2H), 4.47 (q, J=6.5 Hz, 2H), 1.51 (d, J=6.6 Hz, 6H); MS m/z: 549 (M+1).

{2-[2-(1H-sec-butylaminobenzoimidazol-2-yl)-phenyl]-1H-benzoimidazol-5-yl}-sec-butyl-amine $^1$H NMR (300 MHz, $CD_3OD$) δ 8.00–7.95 (m, 2H), 7.71–7.67 (m, 2H), 7.37 (d, J=8.9 Hz, 2H), 6.74 (d, J=8.74 Hz, 2H), 6.70 (s, 2H), 3.38 (q, J=5.7 Hz, 2H), 1.67–1.60 (m, 2H), 1.54–1.46 (m, 2H), 1.17 (d, J=6.5 Hz, 6H), 0.97 (t, J=7.4 Hz, 6H); MS m/z: 453 (M+1).

Example 6

Example 6 provides a further method of elaborating the aniline amine moiety of selected compounds of the invention by converting the amine moiety to the corresponding thiourea. The general method is understood by reference to Scheme 7. Analytical data is provided for exemplary compounds of structure 14.

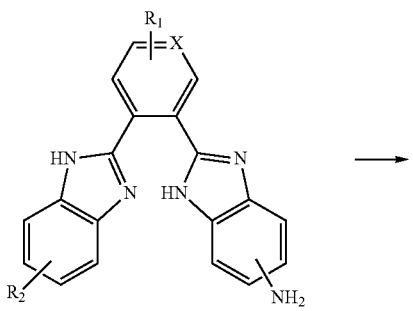

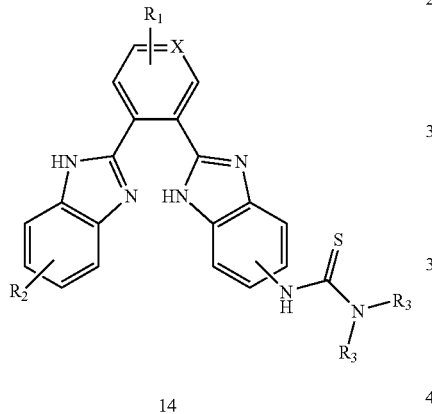

6.1 Formation of Thiourea 14 by the Action of an Isothiocyanate on 10

A solution of 0.059 mmol of 10 and 0.588 mmol of an isothiocyanate in 4 mL of THF was stirred at 50° C. for one day. The crude product was concentrated in vacuo and purified by column chromatography on silica gel to give compound 14.

6.2 Coupling of 10 with 1,1' thiocarbonyldiimidazole

A solution of 0.147 mmol of 10, and 0.368 mmol of 1,1' thiocarbonyldiimidazole was stirred for a half hour, then 0.441 mmol of amine was added. The resulting mixture was stirred for sixteen hours. The crude product was concentrated in vacuo and purified by column chromatography on silica gel to give compound 14.

6.3 Results

Analytical data for exemplary compounds of structure 14 are provided below.

1-(4-Chloro-phenyl)-3-[2-(2-{5-[3-(4-chloro-phenyl)-thioureido]-1H-benzoimidazol-2-yl}-phenyl)-1H-benzoimidazol-5-yl]-thiourea $^1$H NMR (300 MHz, CD$_3$OD) δ 7.98 (dd, J$_1$=3.3 Hz, J$_2$=5.7 Hz, 2H), 7.71 (dd, J$_1$=3.4 Hz, J$_2$=5.9 Hz, 2H), 7.64 (s, 2H), 7.53 (d, J=8.7 Hz, 2H), 7.42 (d, J=8.9 Hz, 4H), 7.31 (d, J=8.8 Hz, 4H), 7.22 (d, J=8.5 Hz, 2H); MS m/z: 679 (M+1).

1-Isopropyl-3-(2-{2-[5-(3-isopropyl-thioureido)-1H-benzoimidazol-2-yl]-phenyl}-1H-benzoimidazol-5-yl)-thiourea $^1$H NMR (300 MHz, CD$_3$OD) δ 7.97 (dd, J$_1$=3.4 Hz, J$_2$=5.9 Hz, 2H), 7.70 (dd, J$_1$=3.3 Hz, J$_2$=5.7 Hz, 2H), 7.55–7.45 (m, 4H), 7.11 (d, J=8.6 Hz, 2H), 4.60–4.45 (m, 2H), 1.18 (d, J=6.6 Hz, 12H); MS m/z: 543 (M+1).

1-Ethyl-3-(2-{2-[5-(3-ethyl-thioureido)-1H-benzoimidazol-2-yl]-phenyl}-1H-benzoimidazol-5-yl)-thiourea $^1$H NMR (300 MHz, CD$_3$OD) δ 7.93 (dd, J$_1$=3.3 Hz, J$_2$=5.6 Hz, 2H), 7.67 (dd, J$_1$=3.3 Hz, J$_2$=5.6 Hz, 2H), 7.53–7.49 (m, 4H), 7.10 (d, J=8.5 Hz, 2H), 3.56 (q, J=7.0 Hz, 4H), 1.15 (t, J=7.1 Hz, 6H); MS m/z: 515 (M+1).

Example 7

Example 7 sets forth a method for preparing compounds of the invention having aryl nitro or aryl amino substituents. The general method is understood by reference to Scheme 8.

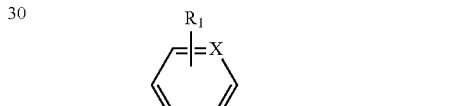

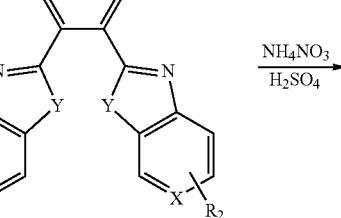

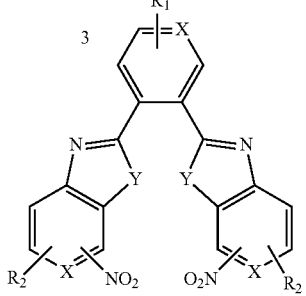

7.1 Nitration of Compound 3

Ammonium nitrate (2.76 mmol) was added to a solution of 1.1 mmol of 3 in 10 mL of $H_2SO_4$. The solution was stirred at 0° C. for one hour. The solution was extracted with dichloromethane and ethyl acetate. The crude product was concentrated in vacuo and purified by column chromatography on silica gel to give compound 16.

7.2 Catalytic Reduction of Compound 16.

A mixture of 0.040 mmol of 16 and 5 mg of Pd/C (10%) in 10 mL of methanol was stirred for four hours under $H_2$ (1 atm). After filtering through celite, the solution was concentrated and the crude product was purified by column chromatography on silica gel to give compound 17.

7.3 Results

Analytical data for exemplary compounds of structure 17 are provided below.

5-fluoro-2-[2-(4-amino-5-fluoro-1H-benzoimidazol-2-yl)-phenyl]-3H-benzoimidazol-4-ylamine $^1$H NMR (300 MHz, CD$_3$OD) δ 7.93 (dd, J$_1$=3.4 Hz, J$_2$=5.7 Hz, 2H), 7.63 (dd, J$_1$=3.3 Hz, J$_2$=5.7 Hz, 2H), 7.20 (d, J=11.1 Hz, 2H), 6.95–6.90 (m, 2H); MS m/z: 377 (M+1).

6-methyl-2-[2-(4-amino-5-methyl-1H-benzoimidazol-2-yl)-phenyl]-3H-benzoimidazol-5-ylamine $^1$H NMR (300 MHz, CD$_3$OD) δ 8.01–7.92 (m, 2H), 7.66–7.61 (m, 2H), 7.25 (s, 1H), 6.94–6.88 (m, 2H), 6.77 (d, J=8.0 Hz, 1H), 2.26 (d, J=3.1 Hz, 6H); MS m/z: 369 (M+1).

6-Chloro-2-[2-(4-amino-5-chloro-1H-benzoimidazol-2-yl)-phenyl]-3H-benzoimidazol-5-ylamine $^1$H NMR (300 MHz, CD$_3$OD) δ 8.02–7.91 (m, 2H), 7.66 (dd, J$_1$=3.4 Hz, J$_2$=5.7 Hz, 2H), 7.48 (s, 1H), 7.07 (d, J=8.5 Hz, 1H), 6.97 (s, 1H), 6.77 (d, J=8.7 Hz, 1H); MS m/z: 409 (M+1).

Example 8

Example 8 sets forth a method of converting an aromatic methyl ether of the invention into the corresponding hydroxyl compound. The general method is understood by reference to Scheme 9.

Scheme 9

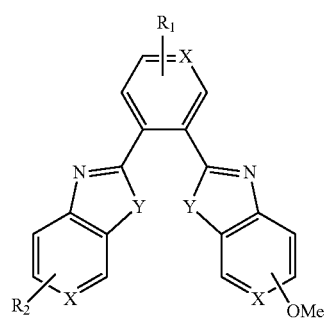

3

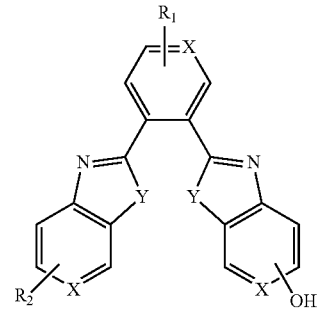

15

8.1 Demethylation of Ether 3 to Alcohol 15

Boron tribromide (18.1 mmol as a 1M solution in dichloromethane) was added to a solution of 1.21 mmol of 3 in 5 mL of dichloromethane at −78° C. The solution was stirred at −78° C. for one hour and then was allowed to stand at −20° C. for two days. LC-MS analysis indicated that all of the starting material was consumed. The solution was poured over saturated NaHCO$_3$ and the mixture was extracted 3 times with ethyl acetate. The combined organic extracts were washed with brine, concentrated in vacuo and purified by column chromatography on silica gel to give compound 15.

8.2 Results

Analytical data for an exemplary compound of structure 15 are provided below.

2-[2-(5-hydroxy-1H-benzoimidazol-2-yl)-phenyl]-1H-benzoimidazol-5-ol $^1$H NMR (300 MHz, CD$_3$OD) δ 7.96 (dd, J$_1$=3.4 Hz, J$_2$=5.8 Hz, 1H), 7.86 (d, J=6.7 Hz, 1H), 7.65 (dd, J$_1$=3.4 Hz, J$_2$=5.7 Hz, 1H), 7.58 (t, J=4.5 Hz, 1H), 7.44–7.36 (m, 2H), 6.89 (s, 2H), 6.77 (d, J=8.7 Hz, 2H); MS m/z: 341 (M−1).

Example 9

Example 9 provides a general synthetic route for converting an aromatic nitrile of the invention into the corresponding amide. The general method is understood by reference to Scheme 10.

Scheme 10

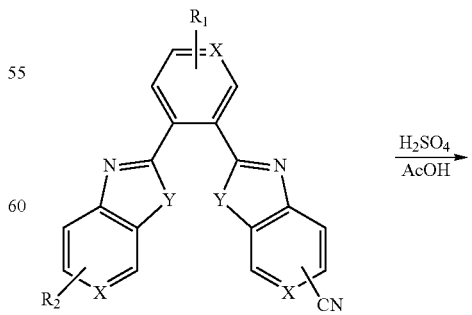

3

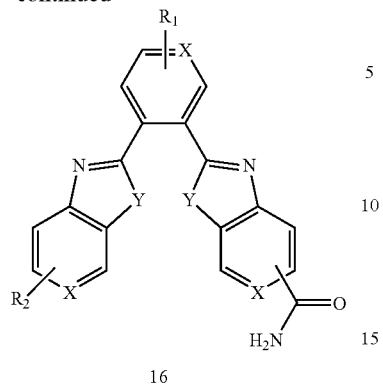

16

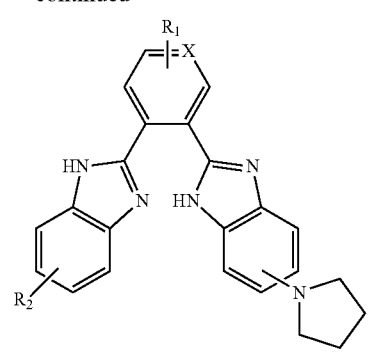

18

9.1 Conversion of Nitrile 3 to Amide 16

A solution of 0.111 mmol of 3 in 2 mL of a 1:1 mixture $H_2SO_4$/AcOH was heated for six hours at 120° C. The solution was cooled to room temperature and stirred for sixteen hours. LC-MS analysis indicated that all starting material was consumed. The solution was quenched with $NH_4OH$ (aq.). After diluting the residue with methanol, the inorganic solid was filtered. The solution was concentrated in vacuo and purified by column chromatography on silica gel to give compound 16.

9.2 Results

Analytical data for exemplary compounds of structure 16 are provided below.

2-[2-(5-carbamoyl-1H-benzoimidazol-2-yl)-phenyl]-1H-benzoimidazole-5-carboxylic acid amide MS m/z: 397 (M+1).

Example 10

Example 10 sets forth a general method for converting the aniline amine moieties of the compounds of the invention to heterocyclic derivatives. The general method is understood by reference to Scheme 11.

Scheme 11

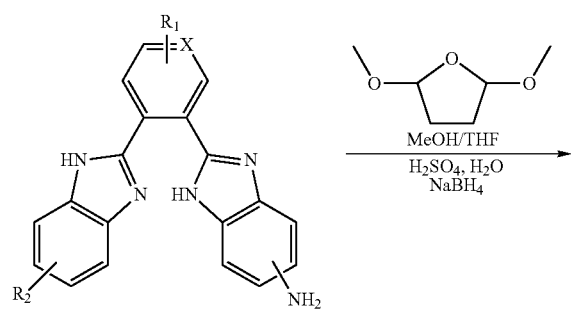

10

10.1 Preparation of Compound 18

Sodium borohydride 10 mg was added to a solution of 0.083 mmol of 10, 0.1 mL of $H_2SO_4$ (con), 0.1 mL of water, and 0.05 mL of 2,5-dimethoxytetrahydrofuran in 2 mL of 1:1 methanol/THF. The solution was stirred for three hours. LC-MS analysis indicated that all starting material was consumed. Then solvent was removed under vacuum. The residue was dissolved in ethyl acetate and washed with saturated $NaHCO_3$ and brine. The crude product was concentrated in vacuo and purified by column chromatography on silica gel to give compound 18.

10.2 Results

Analytical data for exemplary compounds of structure 11 are provided below.

{2-[2-(1H-Benzoimidazol-2-yl)-phenyl]-1H-benzoimidazol-5-yl}-pyrrolidine MS m/z: 380 (M+1).

Example 11

Assay for Compound Activity Towards hSK Channels

Cells expressing small conductance, calcium activated potassium channels, such as SK-like channels were loaded with $^{86}Rb^+$ by culture in media containing $^{86}RbCl$. Following loading, the culture media was removed and the cells were washed in EBSS to remove residual traces of $^{86}Rb^+$. Cells were preincubated with drug (0.01–30 μM in EBSS) and then $^{86}Rb^+$ efflux was stimulated by exposing cells to EBSS solution supplemented with a calcium ionophore, such as ionomycin, in the continued presence of the drug. After a suitable efflux period, the EBSS/ionophore solution was removed from the cells and the $86Rb^+$ content was determined by Cherenkov counting (Wallac Trilux). Cells were then lysed with a SDS solution and the $^{86}Rb^+$ content of the lysate was determined. Percent $^{86}Rb^+$ efflux was calculated according to Equation 1:

$$(^{86}Rb^+ \text{ content in EBSS}/(^{86}Rb^+ \text{ content in EBSS} + {}^{86}Rb^+ \text{ content of the lysate})) \times 100 \quad (1)$$

What is claimed is:

1. A compound having the formula:

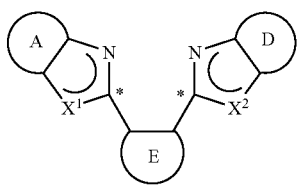

wherein
A and E are independently selected from substituted or unsubstituted phenyl, and substituted or unsubstituted pyridyl ring systems, wherein said substituted phenyl ring system A is substituted with a member selected from substituted or unsubstituted alkyl, substituted or unsubstituted aryl, substituted or unsubstituted heteroaryl, $NH_2$, alkyl amines, aryl amines, carboxyl, $C(O)NH_2$, alkyl amides, aryl amides, sulfonamides, thioureas, alkoxy, carbamate, ester, hydroxy, imides and combinations thereof;

D is selected from substituted phenyl, and substituted or unsubstituted pyridyl ring systems, wherein said substituted phenyl ring system D is substituted with a member selected from substituted alkyl, substituted or unsubstituted aryl, substituted or unsubstituted heteroaryl, $NH_2$, alkyl amines, aryl amines, carboxyl, $C(O)NH_2$, alkyl amides, aryl amides, sulfonamides, thioureas, alkoxy, carbamate, ester, hydroxy, imides and combinations thereof;

the curved line is selected from a double bond between C* and N, a double bond between C* and $X^1$, and a double bond between C* and $X^2$;

$X^1$ and $X^2$ are independently selected from $N(R^1)$, $NHC(R^2)$, $SCR^3$, $OC(R^4)$, and $C(R^5)$; and wherein
$R^1$, $R^2$, $R^3$, $R^4$ and $R^5$ are members independently selected from the group consisting of H, substituted or unsubstituted alkyl and substituted or unsubstituted heteroaryl.

2. The compound according to claim 1, having the formula:

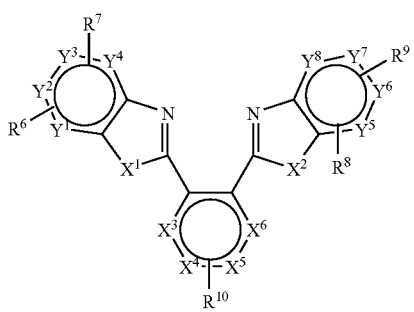

in which
$X^3$, $X^4$, $X^5$, $X^6$, $Y^1$, $Y^2$, $Y^3$, $Y^4$, $Y^5$, $Y^6$, $Y^7$, and $Y^8$ are members independently selected from $C(R^{11})$ and N, with the proviso that no more than two of $Y^1$, $Y^2$, $Y^3$, and $Y^4$ are N, and no more than two of $Y^5$, $Y^6$, $Y^7$, and $Y^8$ are N;

$R^6$, $R^7$, $R^8$, $R^9$, and $R^{11}$ are members independently selected from H, $NH_2$, alkyl amines, aryl amines, carboxyl, $C(O)NH_2$, alkyl amides, aryl amides, sulfonamides, thioureas, esters, alkoxy, carbamate, hydroxy, substituted alkyl, substituted or unsubstituted aryl, substituted or unsubstituted heteroaryl, ketone and combinations thereof, and $R^6$ and $R^7$ are optionally joined to form a ring having from 4 to 8 members, and $R^8$ and $R^9$ are optionally joined to form a ring having from 4 to 8 members; and $R^{10}$ is a member selected from the group consisting of H, OH, $NH_2$, halogen, substituted or unsubstituted alkyl, substituted or unsubstituted aryl, substituted or unsubstituted heteroaryl, substituted or unsubstituted heterocycloalkyl, and substituted or unsubstituted arylalkyl groups.

3. The compound according to claim 2 having the formula:

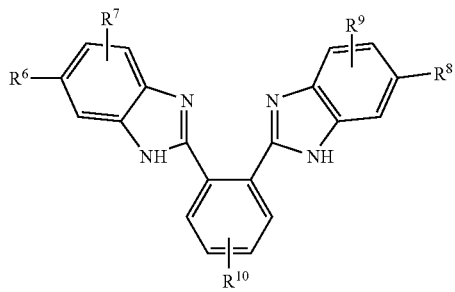

in which
$R^6$, $R^7$, $R^8$, and $R^9$ are members independently selected from the group consisting of H, substituted alkyl, substituted or unsubstituted aryl, substituted or unsubstituted heteroaryl, $C(O)R^{12}$ and $NR^{13}R^{14}$, with the proviso that no more than one of $R^6$ and $R^7$ is H and if one of $R^6$ and $R^7$ is $NH_2$, neither $R^8$ nor $R^9$ is $NH_2$, wherein
$R^{12}$ is a member selected from the group consisting of H, substituted or unsubstituted alkyl, $OR^{18}$, and $NR^{19}R^{20}$, wherein
$R^{18}$, $R^{19}$ and $R^{20}$ are members independently selected from the group consisting of H and substituted or unsubstituted alkyl, and $R^{19}$ and $R^{20}$ together with the nitrogen to which they are attached are optionally joined to form a ring having from 4 to 8 members;

$R^{13}$ and $R^{14}$ together with the nitrogen to which they are bound are optionally joined together into a ring and are members independently selected from the group consisting of H, substituted or unsubstituted alkyl, $C(O)NR^{15}R^{16}$, $C(S)NR^{15}R^{16}$, $S(O)_2R^{17}$, $C(O)R^{17}$, and $C(O)OR^{17}$ wherein R[15] and R[16] are members independently selected from the group consisting of H, substituted or unsubstituted alkyl, substituted or unsubstituted heteroalkyl, substituted or unsubstituted aryl and substituted or unsubstituted heteroaryl, and together with the nitrogen to which they are attached are optionally joined into a ring having from 4 to 8 members;

R[17] is a member selected from the group consisting of substituted or unsubstituted alkyl, substituted or unsubstituted heteroalkyl, substituted or unsubstituted aryl and substituted or unsubstituted heteroaryl; and R[10] is a member selected from the group consisting of H, OH, $NH_2$, halogen and substituted or unsubstituted alkyl groups.

4. The compound according to claim 3, wherein R[6], R[7], R[8], and R[9] are members independently selected from the group:

H, $NH_2$, substituted alkyl, substituted or unsubstituted aryl, substituted or unsubstituted heteroaryl, NHC(O)—($C_1$–$C_{10}$)alkyl; $NHS(O)_2$—($C_1$–$C_{10}$)alkyl, NHC(S)NH—($C_1$–$C_{10}$)alkyl, NHC(O)O—($C_1$–$C_{10}$)alkyl, NHC(O)NH—($C_1$–$C_{10}$)alkyl with the proviso that both R[6] and R[8] are not H.

5. A composition comprising a pharmaceutically acceptable excipient and a compound of the formula:

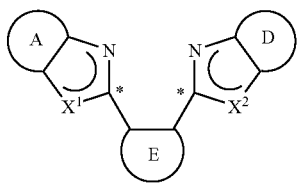

in which

A, D and B are independently selected from substituted or unsubstituted aryl, and substituted or unsubstituted heteroaryl ring systems;

X[1] and X[2] independently represent NR[1], S, O, NHC(R[2]), SC(R[3]), OC(R[4]), and C(R[5]); and R[1], R[2], R[3], R[4], and R[5] are members independently selected from the group consisting of H and substituted or unsubstituted alkyl, substituted or unsubstituted arylalkyl and substituted or unsubstituted heteroaryl.

6. The composition according to claim 5, wherein said ring systems A, D and E are independently selected from substituted or unsubstituted phenyl and substituted or unsubstituted pyridyl ring systems.

7. The composition according to claim 6, wherein said substituted phenyl ring systems A and D are substituted with a member selected from $NH_2$, alkyl amines, aryl amines, carboxyl, esters, $C(O)NH_2$, alkyl amides, aryl amides, sulfonamides, thioureas, alkoxy, carbamate, ether, hydroxy, imides and combinations thereof.

8. The composition according to claim 5, having the formula:

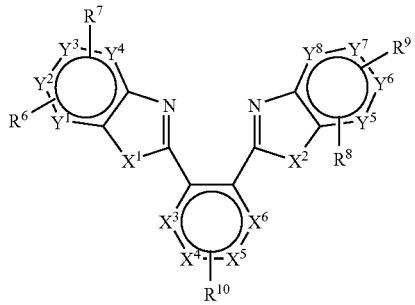

in which

X[3], X[4], X[5], X[6], Y[1], Y[2], Y[3], Y[4], Y[5], Y[6], Y[7], and Y[8] are members independently selected from C(R[11]) and N, with the proviso that no more than two of Y[1], Y[2], Y[3], and Y[4] are N, and no more than two of Y[5], Y[6], Y[7], and Y[8] are N;

R[6], R[7], R[8], R[9] and R[11] are members independently selected from H, $NH_2$, alkyl amines, aryl amines, carboxyl, $C(O)NH_2$, alkyl amides, aryl amides, sulfonamides, thioureas, esters, alkoxy, carbamate, ether, hydroxy, substituted or unsubstituted alkyl, substituted or unsubstituted aryl, substituted or unsubstituted heteroaryl, ketone and combinations thereof, and R[6] and R[7] are optionally joined to form a ring having from 4 to 8 members, and R[8] and R[9] are optionally joined to form a ring having from 4 to 8 members; and R[10] is a member selected from the group consisting of H, OH, $NH_2$, halogen, substituted or unsubstituted alkyl, substituted or unsubstituted aryl, substituted or unsubstituted heteroaryl, substituted or unsubstituted heterocycloalkyl, and substituted or unsubstituted arylalkyl groups.

9. The composition according to claim 8 having the formula:

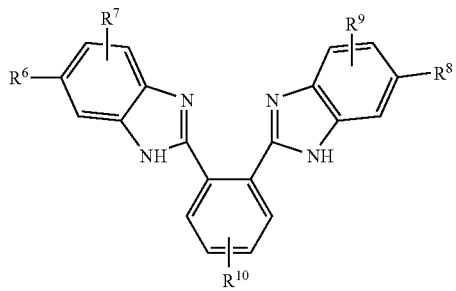

in which

R[6], R[7], R[8,] and R[9] are members independently selected from the group consisting of H, substituted or unsubstituted alkyl, substituted or unsubstituted aryl, substituted or unsubstituted heteroaryl, C(O)R[12] and NR[13]R[14], with the proviso that no more than one of R[6] and R[7] is H and if one of R[6] and R[7] is $NH_2$, neither R[8] nor R[9] $NH_2$, wherein
- $R^{12}$ is a member selected from the group consisting of H, substituted or unsubstituted alkyl, $OR^{18}$, and $NR^{19}R^{20}$, wherein
  - $R^{18}$, $R^{19}$ and $R^{20}$ are members independently selected from the group consisting of H and substituted or unsubstituted alkyl, and $R^{19}$ and $R^{20}$ together with the nitrogen to which they are attached are optionally joined to form a ring;
- $R^{13}$ and $R^{14}$ together with the nitrogen to which they are bound are optionally joined together into a ring and are members independently selected from the group consisting of H, substituted or unsubstituted alkyl, $C(O)NR^{15}R^{16}$, $C(S)NR^{15}R^{16}$, $S(O)_2R^{17}$, $C(O)R^{17}$, and $C(O)R^{17}$ wherein
  - $R^{15}$ and $R^{16}$ are members independently selected from the group consisting of H, substituted or unsubstituted alkyl, substituted or unsubstituted heteroalkyl, substituted or unsubstituted aryl and substituted or unsubstituted heteroaryl, and together with the nitrogen to which they are attached are optionally joined into a ring having from 4 to 8 members;
  - $R^{17}$ is a member selected from the group consisting of substituted or unsubstituted alkyl, substituted or unsubstituted heteroalkyl, substituted or unsubstituted aryl and substituted or unsubstituted heteroaryl; and
- $R^{10}$ is a member selected from the group consisting of H, OH, $NH_2$, halogen and substituted or unsubstituted alkyl groups.

10. The composition according to claim 9, wherein $R^5$, $R^6$, $R^7$, and $R^8$ are members independently selected from the group:

H, $NH_2$, substituted or unsubstituted alkyl, substituted or unsubstituted aryl, substituted or unsubstituted heteroaryl, $NHC(O)$—$(C_1$–$C_{10})$alkyl; $NHS(O)_2$—$(C_1$–$C_{10})$alkyl, $NHC(S)NH$—$(C_1$–$C_{10})$alkyl, $NHC(O)O$—$(C_1$–$C_{10})$alkyl, $NHC(O)NH$—$(C_1$–$C_{10})$alkyl with the proviso that both $R^5$ and $R^7$ are not H.

* * * * *